US007326954B2

(12) United States Patent
Wybourne et al.

(10) Patent No.: US 7,326,954 B2
(45) Date of Patent: *Feb. 5, 2008

(54) SCAFFOLD-ORGANIZED METAL, ALLOY, SEMICONDUCTOR AND/OR MAGNETIC CLUSTERS AND ELECTRONIC DEVICES MADE USING SUCH CLUSTERS

(75) Inventors: Martin N. Wybourne, Hanover, NH (US); James E. Hutchison, Eugene, OR (US)

(73) Assignee: State of Oregon Acting By and Through the State Board of Higher Education on Behalf of the University of Oregon, Eugene, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/816,603

(22) Filed: Apr. 2, 2004

(65) Prior Publication Data

US 2004/0203074 A1  Oct. 14, 2004

Related U.S. Application Data

(63) Continuation of application No. 10/013,334, filed on Nov. 5, 2001, now abandoned, which is a continuation of application No. 09/085,390, filed on May 27, 1998, now abandoned.

(60) Provisional application No. 60/047,804, filed on May 27, 1997.

(51) Int. Cl.
*H01L 51/05* (2006.01)
(52) U.S. Cl. .................. 257/40; 977/705; 977/779; 977/784
(58) Field of Classification Search .............. 435/6, 435/7.1, 287.2; 257/40; 977/705, 779, 784
See application file for complete search history.

(56) References Cited

U.S. PATENT DOCUMENTS

| 4,522,932 | A   |   | 6/1985  | Mitchell, III            |
|-----------|-----|---|---------|--------------------------|
| 5,082,627 | A   | * | 1/1992  | Stanbro ........... 422/82.01 |
| 5,242,877 | A   |   | 9/1993  | Dobson et al.            |
| 5,389,401 | A   |   | 2/1995  | Gordon                   |
| 5,521,289 | A   | * | 5/1996  | Hainfeld et al. ....... 530/391.5 |
| 5,536,858 | A   |   | 7/1996  | Lalonde et al.           |
| 5,578,248 | A   |   | 11/1996 | Hattori et al.           |
| 5,629,213 | A   | * | 5/1997  | Kornguth et al. ......... 436/518 |
| 5,952,172 | A   |   | 9/1999  | Meade et al.             |
| 6,121,425 | A   |   | 9/2000  | Hainfeld et al.          |
| 6,159,620 | A   | * | 12/2000 | Heath et al. ............ 428/615 |
| 6,872,971 | B2  | * | 3/2005  | Hutchinson et al. ........ 257/40 |

FOREIGN PATENT DOCUMENTS

EP  WO 98/53841  12/1998

WO  WO 9853841  A1  * 12/1998

OTHER PUBLICATIONS

Allivastos et al., Nature vol. 382 Aug. 15, 1996 pp. 609-611.*
Peschel et al., Angew. Chem. Int. Ed. Engl. 1995 vol. 34 No. 13/14 pp. 1442-1443.*
Clarke et al., J. Vac. Sci. Tech. B vol. 15(6) Nov./Dec. 1997 pp. 2925-2929.*
Andres et al.,Science vol. 273 Sep. 20, 1996 pp. 1690-1693.*
Grabar et al., Analytical Chemistry vol. 67, No. 4 (Feb. 15, 1995) pp. 735-743.*
Templeton et al., J. Am. Chem. Soc. 1998, vol. 120, pp. 4845-4849.*
Bain et al., J. Am. Chem. Soc. 1989, vol. 111, pp. 321-335.*
O'Konski, C., et al., "Electric Properties of Macromolecules, IV. Determination of Electric and Optical Parameters From Saturation of Electric Birefringence in Solutions," *J. Phys. Chem.* 63: 1558-1565, 1959.
Itou, S., "Reorientation of Poly-γ-Benzyl L-Glutamata Liquid Crystals in an Electric Field," *Jpn. J. Appl. Phys.* 24: 1234-1235, 1985.
Geerligs, L., et al., Frequency-Locked Turnstile Device for Single Electrons, *Phys. Rev. Lett.* 64: 2691-2694, 1990.
Schmid, G., Hexachlorododecakis (triphenylphosphine) pentapentacontagold, $Au_{55}[P(C_6H_5)_3]_{12}Cl_6$, *Inorg. Syn.* 27: 214-218, 1990.
Pothier, H., et al., Single-Electron Pump Based on Charging Effects,: *Europhys. Lett.* 17: 249-254, 1992.
Whitesell, J., et al., "Directionally Aligned Helical Peptides on Surfaces," *Science* 261: 73-76, 1993.
Yano, K., et al., "Transport Characteristics of Polycrystalline-Silicon Wire Influenced by Single-Electron Charging at Room Temperature," *Appl. Phys. Lett.* 67: 828-830, 1995.
Grabar, K., et al., "Preparation and Characterization of Au Colloid Monolayers," *Anal. Chem.* 67: 735-743, 1995.
Oi, J., et al., "Ligation of Triangles Built from Bulged 3-Arm DNA Branched Junctions," *J. Am. Chem. Soc.* 118: 6121-6130, 1996.
Andres, R., et al., "Self-Assembly of a Two-Dimensional Superlattice of Molecularly Linked Metal Clusters," *Science* 273: 1690-1693, 1996.

(Continued)

*Primary Examiner*—Mark L. Shibuya
(74) *Attorney, Agent, or Firm*—Klarquist Sparkman, LLP

(57) ABSTRACT

A method for forming arrays of metal, alloy, semiconductor or magnetic clusters is described. The method comprises placing a scaffold on a substrate, the scaffold comprising molecules selected from the group consisting of polynucleotides, polypeptides, and perhaps combinations thereof. Polypeptides capable of forming α helices are currently preferred for forming scaffolds. Arrays are then formed by contacting the scaffold with plural, monodispersed ligand-stabilized clusters. Each cluster, prior to contacting the scaffold, includes plural exchangeable ligands bonded thereto. If the clusters are metal clusters, then the metal preferably is selected from the group consisting of Ag, Au, Pt, Pd and mixtures thereof. A currently preferred metal is gold, and a currently preferred metal cluster is $Au_{55}$ having a radius of from about 0.7 to about 1 nm. Compositions also are described, one use for which is in the formation of cluster arrays. One embodiment of the composition comprises plural monodispersed, ligand-stabilized clusters coupled to a polypeptide.

11 Claims, 11 Drawing Sheets

OTHER PUBLICATIONS

Niemeyer, C., "DNA as a Material for Nanotechnology," *Angew, Chem., Int. Ed. Engl. 136*: 585-587, 1997.

Seeman, N., "DNA Components for Molecular Architecture," *Accounts of Chemical Research* 30: 357-363, 1997.

Braun, E., et al., "DNA-Templated Assembly and Electrode Attachment of a Conducting Silver Wire," *Nature* 391: 775-778, 1998.

Storhoff, J.J.; Mirkin, C.A., "Programmed Materials Synthesis with DNA," *Chem. Rev.* 99: 1849-1862 1999.

Likharev, K.K., "Correlated Discrete Transfer of Single Electrons in Ultrasmall Tunnel Junctions," *IBM J. Res. Dev.* 32: 144-158, 1988.

Alivisatos, A.P., et al., Organization of 'Nanocrystal Molecules' using DNA,: *Nature* 382: 609-611, 1996.

Mirkin, C., et al., "A DNA Based Method for Rationally Assembling Nanoparticles into Macroscopic Materials," *Nature* 382: 607-609, 1996.

Feldheim, D., et al., "Electron Transfer in Self-Assembled Inorganic Polyelectrolyte/Metal Nanoparticle Heterostructures," *J. Am. Chem. Soc.*118: 7640-7641, 1996.

Osifchin, R.G., et al., "Synthesis of a Quantum Dot Superlattice using Molecularly Linked Metal Clusters," *Superlattices and Microstructures* 18: 283-289, 1995.

Peschel, S.; Schmid, G., "First Steps Towards Ordered Monolayers of Ligand-Stabilized Gold Clusters," *Angew Chem. Int. Ed. Engl.* 34: 1442-1443, 1995.

Simon, U., et al., "The Application of $Au_{55}$ Clusters as Quantum Dots," *Angew. Chem. Int. Ed. Engl.* 32: 250-254, 1993.

Schön, G.; Simon, U., "A Fascinating New Field in Colloid Science: Small Ligand-stabilized Metal Clusters and their Possible Application in Microelectronics," *Colloid Polym. Sci.*273: 202-218, 1995.

Andres, R.P., et al., 'Coulomb Staircase' at Room Temperature in a Self-assembled Molecular Nanostructure,: *Science* 272: 1323-1325, 1996.

Brust, M., et al., "Novel Gold-dithiol Nano-networks with Non-metallic Electronic Properties," *Adv. Mater.* 7: 795-797, 1995.

Brown, L.O.; Hutchison, J.E., "Convenient Preparation of Stable, Narrow-Dispersity, Gold Nanocrystals by Ligand Exchange Reactions," *J. Am. Chem. Soc.* 119: 12384-12385, 1997.

Wybourne, M.N. et al., "Coulomb-blockade Dominated Transport in Patterned Gold-Cluster Structures," *Jpn. J. Appl. Phys.*36: 7796-7800, 1997.

Clarke, L.; Wybourne, M.N., "Fabrication and Near-room Temperature Transport of Patterned Gold Cluster Structures," *J. Vac. Sci. Technol. B* 15: 2925-2929, 1997.

\* cited by examiner

US 7,326,954 B2

SCAFFOLD-ORGANIZED METAL, ALLOY, SEMICONDUCTOR AND/OR MAGNETIC CLUSTERS AND ELECTRONIC DEVICES MADE USING SUCH CLUSTERS

CROSS REFERENCE TO RELATED APPLICATIONS

This application is a continuation of U.S. patent application Ser. No. 10/013,334, filed Nov. 5, 2001 now abandoned, which is a continuation of U.S. patent application Ser. No. 09/085,390, filed May 27, 1998, now abandoned, which claims the benefit of the earlier filing date of U.S. Provisional Patent Application No. 60/047,804, filed May 27, 1997, now abandoned. Each of these prior patent applications is incorporated herein by reference.

STATEMENT OF GOVERNMENT RIGHTS

This invention was made with government support under contract numbers N00014-93-0618 and N00014-93-1-1120 awarded by the Department of Defense, Office of Naval Research, and under Grant No. DMR-9705343 awarded by the National Science Foundation. The government has certain rights in this the invention.

FIELD OF THE INVENTION

This invention concerns a method for forming organized arrays of metal, alloy, semiconductor and/or magnetic clusters for use in the manufacture of electronic devices, such as high density memory storage and nanoelectronic devices.

BACKGROUND OF THE INVENTION

Fundamentally new technologies are required to continue increasing device integration density and speed. Conventional metal-oxide semiconductor-field-effect transistors soon will reach fundamental density and speed limits as a result of quantum mechanical tunneling. In order to scale electronic device sizes down to nanometer dimensions, systems containing increasingly fewer numbers of particles must be considered.

The ultimate limit is a system in which the transfer of a single charge quanta corresponds to information transfer or some type of logical operation. Such single electron systems are presently the focus of intense research activity. See, for example, *Single Charge Tunneling, Coulomb Blockade Phenomena in Nanostructures*, edited by H. Grabert and M. H. Devoret, NATO ASI Series B: Physics Vol. 294 (1992). These systems have potential application to nanoelectronic circuits that have integration densities far exceeding those of present day semiconductor technology. See, *Quantum Transport in Ultrasmall Devices*, edited by D. K. Ferry, H. L. Grubin, C. Jacoboni, and A. Jauho, NATO ASI Series B: Physics Vol. 342 (1995).

Single electron transistors based on the concept of Coulomb blockade are one proposed technology for realizing ultra-dense circuits. K. K. Likharev's *Single Electron Transistors: Electrostatic Analogs of the DC SQUIDS,"* IEEE Trans. Magn. 23:1142 (1987); and *IBM J. Res. Dev.* 32:144 (1988). Coulomb blockade is the suppression of single electron tunneling into metallic or semiconductor islands. In order to achieve Coulomb blockade, the charging energy of an island must greatly exceed the thermal energy. To reduce quantum fluctuations the tunneling resistance to the island should be greater than the resistance quantum $h/e^2$. Coulomb blockade itself may be the basis of conventional logic elements, such as inverters. Id.

Equally promising is the fact that the Coulomb blockade effect can be used to pump charges one-by-one through a chain of dots to realize a frequency-controlled current source in which the current is exactly equal to I=ef, where f is the clocking frequency. See, L. J. Geerligs et al.'s *Frequency-locked Turnstile Device for Single Electrons*, Phys. Rev. Lett., 64:2691 (1990); and H. Pothier et al.'s *Single-Electron Pump Based on Charging Effects*, Europhys. Lett. 17:249 (1992). Such turnstile devices are of fundamental interest as highly accurate current standards.

The clocking of charge through an array is also one model of information storage. It is possible that computation may be based on switching of currents rather than charge which, due to the extreme accuracy of single electron current sources, may be more robust towards unwanted fluctuations than single electron transistor-based circuits.

One of the most promising technologies for realizing terabyte memories is founded on the principle of the Coulomb blockade. Yano et al. have demonstrated room temperature operation of single electron devices based on silicon nanocrystals embedded in $SiO_2$. K. Yano et al.'s *Room-Temperature Single Electron Memory*, IEEE Trans. Electron. Devices, 41:1628 (1994); and K. Yano et al.'s *Transport Characteristics of Polycrystalline-Silicon Wire Influenced by Single Electron Charging at Room Temperature*, Appl Phys. Lett., 67:828 (1995). Recently, a fully integrated 8×8 memory array using this technology has been reported. K. Yano et al.'s *Single-Electron-Memory Integrated Circuit for Giga-to-Tera Bit Storage*, IEEE International Solid State Circuits Conference, p. 266-267 (1996).

Microelectronic devices based on the principle of Coulomb blockade have been proposed as a new approach to realizing electronic circuits or memory densities that go beyond the predicted scaling limit for present day semiconductor technology. While the operation of Coulomb blockade devices has been demonstrated, most operate only at greatly reduced temperatures and require sophisticated nanofabrication procedures. The size scales necessary for Coulomb blockade effects at such relatively elevated temperatures of about room temperature impose limits on the number, uniformity and connectivity of quantum dots. As a result, alternative methodologies of nanofabrication need to be investigated and developed.

SUMMARY OF THE INVENTION

The present invention provides a new process for making arrays comprising metal, alloy, semiconductor and/or magnetic clusters. An "array" can be any arrangement of plural such clusters that is useful for forming electronic devices. Two primary examples of arrays are (1) electronic circuits, and (2) arrangements of computer memory elements, both of which can be in one or several planes.

"Clusters" as used herein refers to more than one, and typically three or more, metal, alloy, semiconductor or magnetic atoms coupled to one another by metal-type bonds. Clusters are intermediate in size between single atoms and colloidal materials. Clusters made in accordance with the present invention also are referred to herein as "nanoclusters." This indicates that the radius of each such cluster preferably is from about 0.7 to about 1.0 nm. A primary goal of the present invention is to provide electronic devices that operate at or about room temperature. This is possible if the cluster size is made small enough to meet Coulomb blockade charging energy requirements at room temperature.

While cluster size itself is not dispositive of whether the clusters are useful for forming devices operable at or about room temperature, cluster size is nonetheless quite important. It currently is believed that clusters having radiuses much larger than the maximum value stated above likely will not be useful for forming electronic devices that operate at or about room temperature.

The metal, alloy, semiconductor and/or magnetic clusters are bonded to "scaffolds" to organize the clusters into arrays. "Scaffolds" are any molecules that can be placed on a substrate in predetermined patterns, such as linear bridges between electrodes, and to which clusters can be bonded to provide organized cluster arrays. Without limitation, a preferred group of scaffolds comprise biomolecules, such as polynucleotides, polypeptides, and mixtures thereof. Polypeptides are currently preferred molecules for forming scaffolds, and polypeptides capable of forming a helices are particularly preferred scaffold-forming molecules.

One embodiment of a method for forming arrays of metal, alloy, semiconductor and/or magnetic clusters first involves placing the scaffold on a substrate, most likely in a predetermined pattern. Arrays are formed by contacting the scaffold with plural, monodispersed (clusters of substantially the same size) ligand-stabilized metal, alloy, semiconductor and/or magnetic clusters. If the clusters are metal clusters, then the metal preferably is selected from the group consisting of Ag, Au, Pt, Pd and mixtures thereof. A currently preferred metal is gold, and a currently preferred metal cluster is $Au_{55}$.

Clusters generally are bonded to the scaffold by ligand exchange reactions. Each cluster, prior to contacting the scaffold, includes plural exchangeable ligands bonded thereto. The ligand-exchange reactions involve exchanging functional groups of the scaffold for at least one of the exchangeable ligands bonded to the cluster prior to contacting the scaffold with the clusters. Examples of exchangeable ligands suitable for forming metal clusters in accordance with the invention can be selected from the group consisting of thiols, thioethers (i.e., sulfides), thioesters, disulfides, sulfur-containing heterocycles, 1°, 2° and perhaps 3° amines, pyridines, phosphines, carboxylates, nitriles, hydroxyl-bearing compounds, such as alcohols, and mixtures thereof. Thiols currently are preferred ligands for practicing the present invention.

There are several methods for placing the scaffold onto substrates in predetermined patterns. For example, a first method comprises aligning scaffold molecules in an electrical field created between electrodes on the substrate. It therefore will be appreciated that the scaffold molecules used must have sufficient dipoles to allow them to align between the electrodes. This is one reason why polypeptides that form α helices are preferred. The α helix imparts a sufficient dipole to the polypeptide molecules to allow alignment of the molecules between the electrodes upon formation of an electrical field. One example of a polypeptide useful for forming scaffolds in accordance with the present invention is polylysine.

A second method comprises polymerizing monomers, oligomers (10 amino acids or nucleotides or less) or small polynucleotides or polypeptides into longer molecules on the surface of a substrate. For example, scaffold molecules can be polymerized as a bridge between electrodes on a substrate.

The present invention also provides compositions, one use for which is in the formation of metal and/or semiconductor arrays. A currently preferred embodiment of the composition comprises monodispersed, ligand-stabilized $Au_{55}$ metal clusters bonded to a polypeptide in the shape of or capable of forming an α helix with the metal clusters bonded thereto. The metal clusters have metal-cluster radiuses of from about 0.7 nm to about 1.8 nm, and preferably from about 0.7 nm to about 1.0 nm.

An object of this invention is to provide methods for fabricating one-, two-, and three-dimensional, scaffold-organized metal cluster arrays.

An object of this invention is to provide high density electronic or memory devices that operate on the principle of Coulomb blockade at ambient temperatures.

DETAILED DESCRIPTION OF THE PREFERRED EMBODIMENTS

Figure 1:
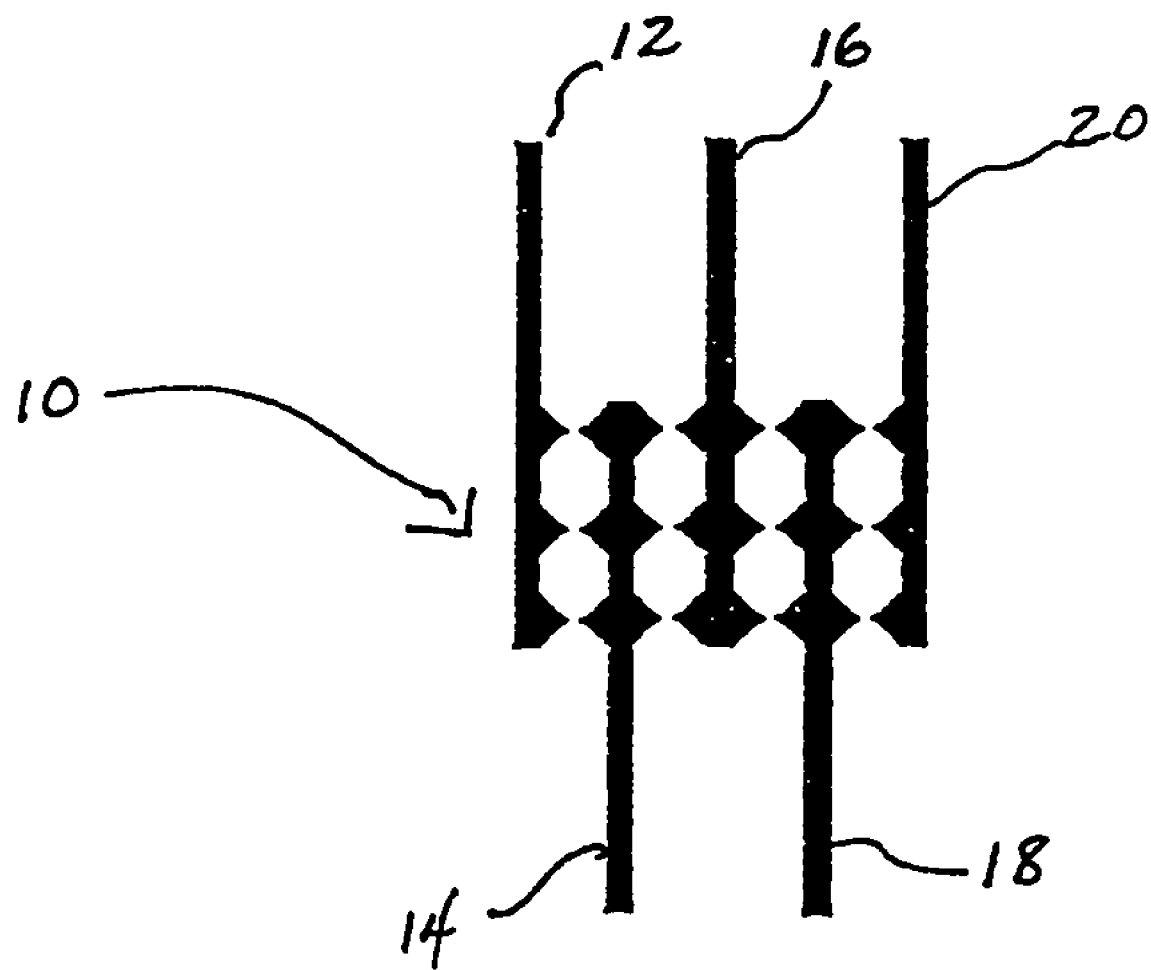
FIG. 1 is a schematic diagram of an interdigitated electrode array having saw-tooth edges.

The general steps used to produce organized arrays comprising metal, alloy, semiconductor and/or magnetic clusters in accordance with the present invention include (1) attaching molecular scaffolds to substrates in predetermined patterns, (2) forming monodispersed, relatively small (i.e., nanocluster size) ligand-stabilized metal, alloy, semiconductor and/or magnetic clusters, (3) coupling the ligand-stabilized clusters to the scaffolds to form organized arrays, (4) coupling electrical contacts to the organized arrays, and (5) using such constructs to form electronic, particulary nanoelectronic, devices. The substrate generally is a metal, glass or semiconductor material.

Currently, most efforts have been directed to developing working devices using metal clusters. Certain of the following passages therefore focus on describing how to make and use devices based on metal cluster arrays. It should be understood, however, that any reference in this application to "metal clusters" or "clusters" typically also refers to alloy clusters, semiconductor clusters, magnetic clusters, and combinations thereof.

Important features of the present invention include the small physical size of the metal clusters, the ligand exchange chemistry and the nature of the ligand shell produced by the ligand exchange chemistry. The small physical size of the metal clusters provides a large Coulomb charging energy. The ligand-exchange chemistry provides a means to taylor the ligand shell for a particular purpose and immobilize the clusters on biomolecules. And, the ligand shell offers a uniform and chemically adjustable tunnel barrier between cluster cores.

The following paragraphs describe the present invention in greater detail.

I. Forming Monodispersed Ligand-Stabilized Clusters

A feature of the present invention is the recognition that monodispersed, relatively small metal clusters can be used to develop electronic devices that operate at or about room temperature based on the Coulomb blockade effect. "Monodispersed" refers to the formation of a population of metal clusters of substantially the same size, i.e., having substantially the same radiuses (or diameters). In contrast, prior-art approaches typically have used polydispersed metal clusters where the size of the metal clusters is not substantially uniform. A completely monodispersed population is one in which the size of the metal clusters is identical. However, complete monodispersity is difficult, if not impossible, to achieve. And complete monodispersity is not required to produce devices operating at room temperature based on the Coulomb blockade effect. Nevertheless, as the dispersity of the cluster population proceeds from absolute monodispersity towards polydispersity the likelihood that the device will operate reliably at room temperature based on the Coulomb blockade effect decreases.

Moreover, as the radius of the metal cluster decreases, the intrinsic capacitance gets smaller. As capacitance gets smaller, the charging energy of the cluster gets larger. Coulomb blockade effects are observed when the charging energy exceeds the thermal energy at room temperature. Prior approaches have used clusters having radiuses generally larger than would be useful for forming devices that operate at room temperature based on the Coulomb blockade effect. In contrast, the present invention forms metal "nanoclusters" having relatively small radiuses. The size requirement for clusters made in accordance with the present invention can be established in at least two ways, (1) by stating absolute radius lengths, and (2) by comparing the radius of the cluster in question to the radius of gold clusters made having magic numbers (see the discussion provided below) of gold atoms.

In terms of absolute numbers, "nanocluster" is defined herein as a cluster having a radius of from about 0.7 nm to about 1.8 nm (7 Å to about 18 Å), preferably from about 0.7 nm to about 1.25 nm (7 Å to about 12.5 Å), and even more preferably from about 0.7 nm to less than or equal to 1.0 nm (7 Å to less than or equal to 10 Å). These radius lengths refer solely to the radius of the metal cluster, and not the radius of the metal cluster and ligand sphere.

With its insulating ligand shell, the diameter of the ligand-stabilized metal cluster can vary. The size of the ligand shell may influence the electron tunneling rate between clusters. Tunneling rate is exponentially related to the thickness of the ligand shell. As a result, the diameter of the ligand shell may be tailored for a particular purpose. It currently is believed that the diameters for ligand-stabilized clusters useful for practicing the present invention should be from about 2.5 nm to about 5 nm. The relatively large metal clusters made previously do not provide a large Coulomb charging energy and do not operate at room temperature, and instead generally only operate at temperatures of from about 50 mK to about 10K.

"Bare" clusters, i.e., those without ligand shells, also may be useful for practicing the present invention. For example, bare clusters can be used to form electrical contacts.

Still another consideration is the distance between the edges of metal cluster cores. It currently is believed that the maximum distance between the edges of cluster cores for clusters useful for practicing the present invention is about 5 mm (50 Å), and ideally is on the order of from about 1 to about 2 nm (10-20 Å).

Originally it was believed that clusters in accordance with the present invention generally should include numbers of atoms that are based on the so-called "geometric magic numbers" of atoms surrounded by a ligand shell. Geometric magic numbers result from the most densely packed arrangement of atoms that form a "sphere." Magic numbers are given by Formula 1 below $$1 + \sum_{n=1}^{k} (10n^2 + 2)1 \qquad \text{Formula 1}$$

where k is an integer that represents the number of shells of metal atoms surrounding a central atom. Noble metal clusters with k=2, 4, 6, 7 and 8 have been synthesized and stabilized by a ligand shell. While clusters having magic numbers of atoms will work to practice the present invention, it has now been determined that magic numbers of atoms likely are not required to provide clusters useful for practicing the present invention.

Solely by way of example, the most likely metals to be used to form ligand-stabilized metal clusters in accordance with the present invention can be selected from the group consisting of silver (Ag), gold (Au), platinum (Pt), palladium (Pd), and mixtures thereof. "Mixtures thereof" refers to having more than one type of metal cluster coupled to a particular scaffold, or different metal clusters bonded to different scaffolds used to form a particular electronic device. It also is possible that metal alloy clusters, e.g., gold/palladium clusters, can be used to form cluster arrays and electronic devices in accordance with the present invention.

Gold is the currently preferred metal for forming ligand-stabilized monodispersed metal clusters. This is because (1) the ligand exchange chemistry for gold nanoclusters and the nature of the ligand shell formed about gold is well understood, (2) $Au_{55}$ has a diameter of about 1.2 nm, which has proved ideal for forming organized metal arrays that exhibit the Coulomb effect at or about room temperature, and (3) it is possible to prepare nearly monodispersed gold clusters without lengthy purification requirements, such as lengthy crystallization processes.

Assuming that magic numbers do provide benefit, the magic numbers of gold, palladium and platinum atoms for use with the present invention are 13, 39, 55, 147 and 309. 55 is the currently preferred magic number (represented as $Au_{55}$, $Pd_{55}$ and $Pt_{55}$). The magic number of silver atoms for silver metal clusters useful for practicing the present invention likely are the same as for gold, but this has not yet been verified.

Semiconductor materials also likely are useful for practicing the present invention. Likely semiconductor materials that can be made into nanoclusters and stabilized with ligand spheres include, without limitation, cadmium selenide, zinc selenide, cadmium sulfide, cadmium tellurite, cadmium-mercury-tellurite, zinc tellurite, gallium arsenide, indium arsenide and lead sulfide.

Magnetic particles also can be used to decorate scaffolds in accordance with the present invention. An example, without limitation, of such magnetic particles is iron oxide ($Fe_2O_3$).

II. Ligands

A. Background

Once a suitable metal, alloy, semiconductor and/or magnetic material is selected for forming nanoclusters, ligands for bonding to the clusters also must be selected. The assembly of clusters into Coulomb blockade structures requires molecular-scale organization of the clusters while simultaneously maintaining the insulating ligand sphere between individual clusters. The clusters also must be coupled to the scaffold in a sufficiently robust manner to allow for fabrication of devices incorporating cluster arrays. This can be accomplished by ligand exchange reactions. The selection of ligands for forming an insulating ligand layer about the cluster and for undergoing ligand exchange reactions therefore is an important consideration. A list of criteria useful for selecting appropriate ligands includes, but may not be limited to, (1) the ligands should be capable of undergoing reactions with the scaffold, such as ligand-exchange, acid-base or intercelation reactions (2) the ligands preferably increase the solubility of the ligand-metal cluster complexes in organic solvents, which helps synthesize metal clusters and perform subsequent reactions, and (3) the ligands selected preferably form well ordered metal-ligand complexes having diameters as stated above.

B. Classes of Ligands

Ligands deemed most suitable for forming metal clusters in accordance with the present invention can be selected, without limitation, from the group consisting of: thiols (RSH); thioethers (also known as sulfides, R—S—R'); thioesters (R—S$_2$H); disulfides (R—S—S—R'); sulfur-containing heterocycles, such as thiophene; 1□, 2□ and perhaps 3□ amines ($RNH_2$, $R_2NH$ and $R_3N$, respectively), particularly 1□ amines; pyridines; phosphines ($R_3P$); carboxylates ($RCO_2^-$); nitriles (RCN); hydroxyl-bearing compounds, such as alcohols (ROH); and mixtures thereof. Additional guidance concerning the selection of ligands can be obtained from Michael Natan et al.'s *Preparation and Characterization of Au Colloid Monolayers*, Anal. Chem., 67:735-743 (1995), which is incorporated herein by reference.

Organic sulfur-containing molecules (e.g., thiols, thioethers, thioesters, disulfides, sulfur-containing heterocycles, and mixtures thereof) currently are the preferred class of ligands. Thiols are the currently preferred type of sulfur-containing ligand for several reasons. For example, thiols have an affinity for gold, which often is formed into electrodes or electrode patterns. Moreover, thiols have been shown to be good ligands for stabilizing gold clusters. And, many thiol-based ligands are commercially available. The thiols form ligand-stabilized metal clusters having a formula $M_x(SR)_n$ wherein M is a metal, R is an alkyl chain or aromatic group, x is a number of metal atoms that provide metal clusters having the characteristics described above, and n is the number of thiol ligands attached to the ligand-stabilized metal clusters.

C. Organic Portion of Ligands

The organic portion of ligands useful for practicing the present invention also can vary. For example, the length of the alkyl chain can be varied to obtain particular features desired in the ligand-stabilized metal clusters. These include the solubility of the metal clusters in solvents used to carry out the present invention and the size and insulating characteristics of the ligand-stabilized metal clusters. Currently, alkyl chains having from about 2 carbon atoms to about 20 carbon atoms are deemed most suitable for practicing the present invention.

Aryl-type ligands, i.e., aromatic groups such as phenyl rings, containing or having sulfur atoms coupled thereto also have been used as ligands for forming ligand-stabilized metal clusters. For example, mercaptobiphenyl (HS-phenyl-phenyl) has been used to form ligand-stabilized gold clusters. The aromatic rings of such compounds likely will be functionalized to include functional groups capable of reacting with the scaffold molecules. For example, the aromatic rings might include acidic groups, such as carboxylic acids, for acid-base reactions with functional groups of the scaffold molecules, such as amines.

Aromatic ligands are quite useful for producing rigid arrays, which helps stabilize the electron transport properties. For this reason, aryl ligands currently are considered preferred ligands for practicing the present invention. But, small alkyl groups, such as thioproprionic acid, also provide rigid ligand systems.

Ligands that intercalate into DNA also can be used. This allows a means for attaching the metal clusters to DNA molecules. Typically, the DNA intercalating ligands include rigid π systems. Examples of such DNA intercalating ligands include, without limitation, anthraquinone and phenanthridinium derivatives. The DNA intercalating ligands also can be made DNA-sequence dependent. Thus, DNA having particular sequences can be used as a scaffold that is intercelated at predetermined portions of the scaffold. This provides a method for designing the spacing between metal clusters. The intercalating ligands also can be photo-crosslinked to provide a more rigid system.

D. General Method for Producing Ligand-Stabilized Metal Clusters

The general approach to making ligand-stabilized metal clusters first comprises forming monodispersed metal clusters having displaceable ligands. This can be accomplished by directly forming monodispersed metal clusters having the appropriate ligands attached thereto, but is more likely accomplished by first forming monodispersed, ligand-stabilized metal clusters which act as precursors for subsequent ligand-exchange reactions with ligands deemed more useful for practicing the present invention.

One example, without limitation, of a monodispersed gold cluster that has been produced and which is useful for subsequent ligand-exchange reactions with the ligands listed above is $Au_{55}[P(C_6H_5)_3]_{12}Cl_6$. A procedure for making monodispersed $Au_{55}[P(C_6H_5)_3]_{12}Cl_6$ nanoclusters is provided by G. Schmid's *Hexachlorodecakis(triphenylphos-*

*phine)-pentapentacontagold*, $Au_{55}[P(C_6H_5)_3]_{12}Cl_6$, *Inorg. Syn.*, 27:214-218 (1990). Schmid's publication is incorporated herein by reference. Schmid's synthesis involves the reduction of $AuCl[Ph_3]_6$. Example 1 below also discusses the synthesis of $Au_{55}[P(C_6H_5)_3]_{12}Cl_6$. One advantage or Schmid's synthesis is the relatively small size distribution of clusters produced by the method, e.g., 1.4±0.4 nm.

Once ligand-stabilized monodispersed metal clusters are obtained, such clusters can be used for subsequent ligand-exchange reactions, as long as the ligand-exchange reaction is readily facile and produces monodispersed metal clusters. Prior to the present invention it was not appreciated that the $Au_{55}[P(C_6H_5)_3]_{12}Cl_6$ clusters could be used to form nearly monodispersed derivatives by ligand-exchange chemistry. In fact, some literature reports indicated that it was difficult, if not impossible, to form linked metal clusters by ligand-exchange reactions. See, for example, Andres et al.'s *Self-Assembly of a Two-Dimensional Supperlattice of Molecularly Linked Metal Clusters, Science*, 273:1690-1693 (1996).

To perform ligand-exchange reactions, a reaction mixture is formed comprising the metal cluster having exchangeable ligands attached thereto and the ligands to be attached to the metal cluster, such as thiols. A precipitate generally forms upon solvent removal, and this precipitate is then isolated by conventional techniques. See, Examples 2 and 3 for further details concerning the synthesis of ligand-stabilized metals.

III. Molecular Scaffolds

A. Background

Metal clusters produced as stated above are coupled to molecular scaffolds. "Coupling" as used herein refers to some interaction between the scaffold and the ligand-stabilized metal clusters such that the metal clusters become associated with the scaffold. Associated may mean covalently bound, but also can include other molecular associations, such as electrostatic interactions. "Coupling" most typically refers to attaching clusters to the scaffolds by either (1) ligand exchange reactions where functional groups of the scaffold molecules, such as sulfur-containing functional groups or amines, exchange with ligands forming the metal-ligand complex, (2) acid-base type reactions between the ligands and molecules of the scaffold, or (3) intercelation of a ligand into a DNA helix.

B. Scaffolds Comprising Biomolecules

To form useful devices, the scaffolds must be disposed on a substrate in predetermined patterns to which electric contacts can be made. The scaffolds of the present invention can comprise biomolecules, such as polynucleotides, polypeptides and mixtures thereof, and hence are most appropriately referred to as biomolecular scaffolds. There is some precedent for using polynucleotides for forming molecular scaffolds. See, for example, C. A. Mirkin et al.'s *A DNA-Based Method for Rationally Assembling Nanoparticles into Macroscopic Materials*, Nature, 382:607 (1996); and A. P. Alivisatos et al.'s *Organization of 'Nanocrystal Molecules' using DNA*, Nature, 382:609 (1996). Each of these references is incorporated herein by reference. Polynucleotides provide a different spacing between metal clusters than do polypeptides. Thus, spacing between metal clusters can be varied by changing the nature of the scaffold. Polypeptides may provide the best spacing for the formation of electronic devices operating at room temperature based on the Coulomb blockade effect.

Preferred polypeptides are those polypeptides that form α helical secondary structures. Certain peptides, although attractive candidates from the standpoint of being stabilizing ligands for the metal clusters, do not form α helice. However, many polypeptides do form α helices, and hence are good candidates for forming scaffolds in accordance with the present invention.

It also should be appreciated that the polypeptide can be a "homopolypeptide," defined herein to refer to polypeptides having only one type of amino acid. One example of a homopolypeptide is poly-L-lysine. The free base form of polylysine readily forms an α helix. Moreover, lysine provides a terminal amino group that is oriented favorably in the α helix for ligand exchange reactions with the ligand-stabilized metal clusters. Homopolypeptides generally have been used in the practice of the present invention for several reasons. First, certain homopolypeptides are commercially available, such as polylysine. Second, homopolypeptides provide more predictable α helix formation with the side chains oriented outwardly from the α helix at known, predictable distances. This allows the polypeptide to be designed for a particular purpose.

The peptide also may be a "heteropolypeptide" (having two or more amino acids), or block copolymer-type polypeptides (formed from plural different amino acids with identical amino acids being organized in blocks in the amino acid sequence), as long as such peptides (1) form α helices, and (2) provide functional groups positioned and capable of engaging in ligand exchange reactions with the monodispersed metal clusters.

Most amino acids can be used to form suitable homo- or heteropolypeptides. Examples of particularly suitable amino acids include, but are not limited to, naturally occurring amino acids such as arginine, tyrosine, and methionine; and nonnaturally occurring amino acids such as homolysine and homocysteine.

IV. Placing Scaffolds on Substrates

A. General Discussion

The scaffold simply may be placed on the surface of the substrate, in contrast to more tightly adhering the polypeptide to the substrate such as through electrostatic or covalent bonds. As used herein, the term "substrate" refers to any material, or combination of materials, that might be used to form electronic devices. For example, the substrate might be selected from the group consisting of silicon, silicon nitride, ultraflat glass, metals, and combinations thereof.

Simply placing the scaffold on the surface without considering whether to electrostatically or covalently bind the scaffold to the substrate simplifies the process for making working devices. Placing the scaffold on the surface of the substrate can be accomplished by (1) forming solutions containing the molecular scaffold, (2) placing the solution containing the scaffold onto a substrate, such as by spin coating the solution onto a substrate, and (3) allowing the solvent to evaporate, thereby depositing the solid molecular scaffold onto the substrate surface.

If simple deposition of the scaffold onto the substrate does not produce a sufficiently robust device, then the scaffold might be more tightly coupled to the substrate. One method for accomplishing this is to use compounds that act as adhesives or tethers between the substrate and the molecular scaffold. Which compounds to use as adhesives or tethers depends on the nature of the substrate and the metal cluster. For example, amino-silane reagents may be used to attach molecular scaffolds to the substrate. The silane functional group allows the tether to be coupled to a silicon, glass or gold substrate. This provides a tether having a terminal amino group that can be used to react with the scaffold to tether the scaffold to the substrate. The terminal amino group also can be used as an initiation site for the in situ polymerization of polypeptides using activated amino acids. Another class of tethers particularly useful for attaching polylysine to substrates is the ω-carboxyalkanethiols ($^-O_2C$—R—SH).

B. Organization of Scaffolds on Substrates

There are at least four methods for forming organized molecular arrays, particularly linear arrays, on the surface of substrates. The first comprises depositing dilute solutions of scaffold molecules onto substrates. The second comprises aligning α-helical polypeptides between electrodes. The third comprises growing polypeptide chains between two or more electrodes beginning from an initiation site placed on an electrode. And the fourth comprises forming DNA scaffolds between electrodes. Each of these approaches is discussed below.

1. Deposition from Dilute Solutions

First, isolated molecular scaffolds can be prepared by depositing highly dilute solutions onto substrate surfaces. Alternatively, this can be accomplished by dilution of the molecular scaffold film with an inert, α-helix polypeptide such as poly-γ-benzyl-L-glutamate. See, *Poly(γ-Benzyl-L-Glutamate) and Other Glutamic Acid Containing Polymers*, H. Block (Gordon & Breach, NY) 1983.

2. Aligning Polypeptides in a High Electrical Field

The second, and likely most practical method, for providing a scaffold on a substrate is to align a polypeptide "bridge" in an electrical field produced between two electrodes. FIG. 1 illustrates saw tooth electrodes 10 comprising electrodes 12-20 that are placed on a substrate by conventional methods, such as electron-beam lithography, thermal evaporation, or lift-off techniques. A solution comprising the scaffold molecules is first formed and then applied to the surface of the substrate having the electrode pattern placed thereon, such as a substrate having the electrode pattern of FIG. 1. α-Helical polypeptides self-align (pole) in the presence of an applied magnetic field or electrical field (typically 20 Vcm$^{-1}$). See, S. Itou's *Reorientation of Poly-γ-benzyl-L-glutamate Liquid Crystals in an Electric Field*, Jpn. Appl. Phys., 24:1234 (1985). Presumably this is due to their large diamagnetic anisotropy. See, C. T. O'Konski et al.'s *Electric Properties of Macromolecules IV. Determination of Electric and Optical Parameters From Saturation of Electric Birefringence in Solutions*, J. Phys. Chem., 63:1558 (1959). An electric field is generated between the electrodes, such as the points of the saw tooth illustrated in FIG. 1. This local field between the two points causes the scaffold to align between the points. The solvent is evaporated to provide scaffolds oriented between the electrodes.

Based on the above, it will be apparent that the dipole moment of the scaffold influences whether the polypeptide can be oriented between the two electrodes, and the efficiency of the orientation. This is one reason why a helical polypeptides are a currently preferred polypeptides for forming scaffolds. The hydrogen bonds formed in the α helix all orient in the same direction, thereby imparting a dipole to the secondary α helical structure. It currently is believed that the dipole is primarily the result of the α helix, and not the side chains. As a result, preferred polypeptides for practicing the present invention are those that form α helices.

3. Growing Polypeptides Between Electrodes

In some instances, it may be desirable to use scaffolds to bridge directly between two electrical contacts of interest. This can be accomplished by first placing initiating sites on the electrodes, and then "growing" polypeptides between the initiation sites on the electrodes to form a bridge. One example of how this would be accomplished is to attach a tether to an electrode, the tether having a pendant functional group that is capable of forming peptide bonds when reacted with an activated amino acid. The most likely pendant functional group for this purpose is a 1° amine.

To provide a specific example to illustrate the procedure, a tether comprising an alkyl chain having both a terminal amino group and a terminal sulfhydryl group (i.e., an amino-thiol, HS—R—NH$_2$) is reacted with a gold electrode using conventional chemistry. This covalently attaches the sulfhydryl group of the tether to the metal (i.e., Au—S—R—NH$_2$). The terminal amino group is then used to initiate polymerization of a polypeptide using activated amino acids, perhaps in the presence of an applied field, between the two electrodes. The polymerization is accomplished by supplying activated amino acids for reaction with the primary amine in a chain-growing reaction which serially couples amino acids to the end of the growing chain and regenerates the primary amine for subsequent reaction with another activated amino acid.

Activated amino acids are commercially available and are described in the literature. One example, without limitation, of an activated amino acid for formation of peptide bonds in this manner is N-carboxyanhydride (NCA) amino acids. NCA amino acids react with surface-bound initiator sites (e.g., the primary amino groups) to begin a ring-opening polymerization of the NCA-amino acid. See, J. K. Whitesell et al.'s *Directionally Aligned Helical Peptides on Surfaces*, Science, 261:73 (1993). Whitesell's publication is incorporated herein by reference.

When NCA polymerization is performed under the influence of an electric field applied between two electrodes it is possible to "grow" the polypeptide scaffolds from one electrode to the other. One specific example of an NCA amino acid that can be used for this purpose is that derived from N$_\in$-benzyloxycarbonyl-L-lysine. The amino acid side chains of this compound can be deprotected using trimethylsilyl iodide. Deprotection yields the poly-L-lysine scaffold.

Working embodiments of the present invention generally have used polylysine as the polypeptide useful for forming the molecular scaffold. Polylysine was chosen because it includes a hydrocarbon chain that extends the amino functional group, which can undergo ligand-displacement reactions with the ligand-stabilized metal cluster, out and away from the polypeptide backbone. Thus, two important criteria for selecting polypeptides for use as molecular scaffolds are (1) does the polypeptide form α helices, and (2) do the amino acid side chains provide functional groups that are metal-cluster stabilizing and capable of undergoing ligand-exchange reactions with the ligand-stabilized metal clusters.

4. Forming Polynucleotide Scaffolds

Methods for providing polynucleotide scaffolds also recently have been discovered. See, for example, (1) E. Braun et al., "*DNA Templated Assembly and Electrode Attachment of a Conducting Silver Wire*," Nature, p. 775 (1998); (2) N. Seeman, "*DNA Components for Molecular Architecture*," Accounts of Chemical Research, 30:357 (1997); Qi J., et al. "*Ligation of Triangles Built from Bulged 3-Arm DNA Branched Junctions*," J. Am. Chem. Soc., 118:6121 (1996); and C. Niemeyer et al., "*DNA as a Material for Nanotechnology*," Angewandte Chemie, International Edition in English, 36:585 (1997). Each of these references is incorporated herein by reference. The Braun reference provides a method for positioning a DNA molecule between electrodes spaced by a particular distance, such as about 10 μm. Double stranded DNA, with single stranded sticky ends, and a pair of electrodes that have single stranded DNA attached thereto that is complementary to the sequence of the sticky ends of the DNA are prepared. Annealing the sticky ends to the single-stranded primers allows coupling of double stranded DNA between two electrodes spaced by a known distance.

V. Decorating Scaffolds with Metal Clusters

Figure 2:
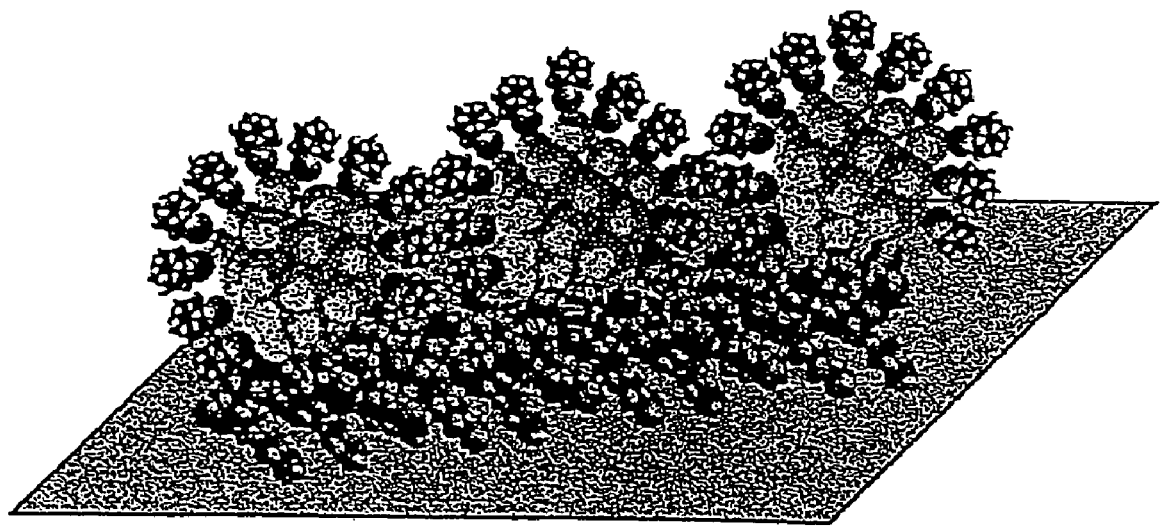
FIG. 2 is a schematic representation of a poly-L-lysine scaffold having thiophenolate-stabilized nanoclusters coupled thereto.

To provide working electronic devices, clusters must be coupled to the scaffolds. FIG. 2 provides a schematic representation of a poly-L-lysine that is "decorated" with metal clusters, i.e., the clusters are coupled to the scaffold. A first consideration is whether to decorate the scaffold with clusters prior to or subsequent to placing the scaffold onto a substrate. Although both of these approaches work, there are some disadvantages with decorating the scaffold with the clusters prior to placing the scaffold on the substrate. This approach places clusters on all surfaces of the polypeptide, even those that come into contact with the underlying substrate. This is undesirable for several reasons. For example, such placement of the clusters might interfere with fixing the decorated scaffold to the substrate. And, it places clusters in locations in which they are not needed, and hence uses more valuable monodispersed clusters than needed.

Based on the above, a method which first places the scaffolds onto a substrate, and subsequently decorates the scaffold with clusters is a currently preferred approach. This can be accomplished by first forming a solution comprising the ligand-stabilized monodispersed clusters using a solvent that does not dissolve the scaffold. Candidate solvents for this purpose include, without limitation, dichloromethane and hexanes. The ligand-stabilized clusters are then introduced onto the scaffold and allowed to undergo reactions with the scaffold molecules, such as ligand-exchange or acid-base type reactions, thereby coupling the ligand-stabilized clusters to the scaffold. See, Example 4 for further details concerning decorating scaffolds with clusters.

The present approach to producing decorated scaffolds also allows for good lateral definition, which is a key feature of the present invention. "Lateral definition" refers to the width of an array. Prior to the present invention, the state of technology was capable of producing lines having a width of about 300 Å. With the present invention, lateral resolution is much improved, and is on the order of about 10 Å. In addition, branched polypeptides offer the possibility of introducing control electrodes and interconnects at the molecular level.

VI. Ultrafast, Ultrahigh Density Switching Devices

This section discusses the steps required to use the decorated molecular scaffolds of the present invention to produce ultrafast, ultrahigh density switching devices. First, a substrate is selected and cleaned. One example of a substrate is a silicon nitride chip or wafer. On top of this substrate would be placed electrical contacts. This could be accomplished using known technologies, such as lithography or thermal evaporation of a metal, such as gold.

Once a substrate is obtained having the electrical contacts placed thereon, a scaffold is then placed on the surface using the techniques described above. Thereafter, the substrate with scaffold is treated with monodispersed, ligand-stabilized clusters to attach such clusters to the scaffold. The organization of scaffold likely determines the particular device being made.

For a switching device, analogous to a transistor, saw tooth electrical contacts, such as those shown in FIG. 1, are deposited onto a substrate and a scaffold then oriented therebetween. This provides two arms of a transistor. A capacitance contact required to provide the third arm of a transistor is imbedded in the substrate underneath the molecular scaffold. Direct electrical contact with this "gate" imbedded in the substrate is not actually required.

Figure 3:
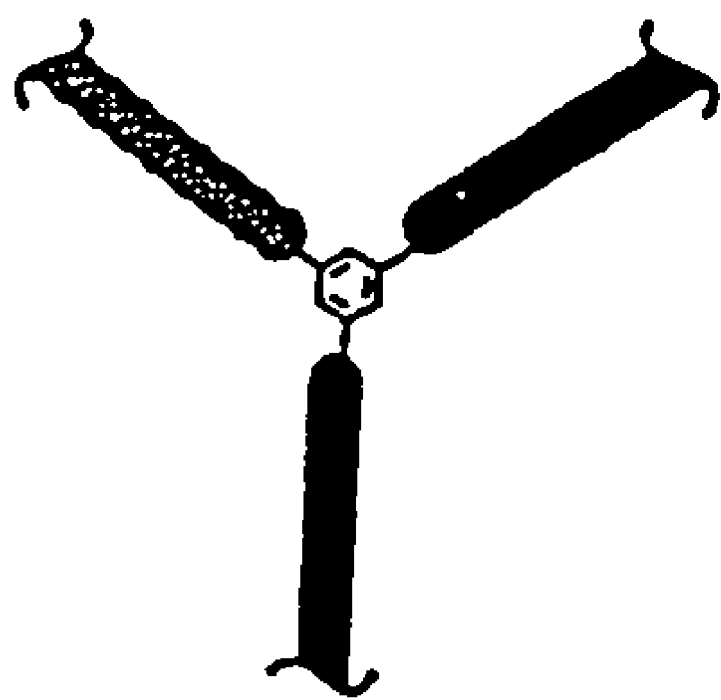
FIG. 3 is a schematic representation of one method for incorporating gate electrodes at the molecular level.

Alternatively, a third contact arm could be incorporated into the template. FIG. 3 is a schematic representation of a scaffold useful for this purpose. For example, a polypeptide of a particular length, e.g., a 25-mer or 50-mer, could first be coupled to an electrode. A branching portion of the scaffold could then be attached, thereby forming an electrical arm, or plural such arms, for further providing single or multiple gate electrodes to the template. The scaffold is then coupled between two electrodes subsequent to the formation of this contact arm, or arms.

The method of the present invention can be used to form a variety of standard circuit components to implement Boolean logic functions. These circuit components include, but are not limited to, AND, NAND, NOR, OR and Exclusive OR gates. Additionally, multiplexers and muliplexer-based circuits can be created and used to implement Boolean logic functions.

VII. EXAMPLES

The following examples are provided to illustrate certain particular features of the present invention. These examples should not be construed to limit the invention to the particular features described.

Example 1

This example describes the syntheses of $Au_{55}(PPh_3)_{12}Cl_6$. $Au[P(C_6H_5)_3]Cl$ was obtained from Aldrich Chemical Company. This compound was reduced using diborane ($B_2H_6$), which was produced in situ by the reaction of sodium borohydride ($NaBH_4$) and borontrifluoride etherate [$BF_3.O(C_2H_5)$]. $Au[P(C_6H_5)_3]Cl$ was combined with diborane in benzene to form $Au_{55}(PPh_3)_{12}Cl_6$. $Au_{55}(PPh_3)_{12}Cl_6$ was purified by dissolution in methylene chloride followed by filtration through Celite. Pentane was then added to the solution to precipitate a black solid. The mixture was filtered and the solid was dried under reduced pressure to provide $Au_{55}(PPh_3)_{12}Cl_6$ in approximately 30% yield.

Example 2

This example describes the synthesis of $Au_{55}(SC_{18}H_{37})_{26}$. Dichloromethane (≈10 ml), $Au_{55}(PPh_3)_{12}Cl_6$ (20.9 mg) and octadecylthiol (23.0 mg) were combined in a 25 ml round bottom. A black solution was produced, and this solution was stirred under nitrogen at room temperature for 36 hours. The solvent was then removed under reduced pressure and replaced with acetone. This resulted in the formation of a black powder suspension. The solid was then isolated by vacuum filtration and washed with acetone (10×5 ml). After the final wash, the solid was redissolved in hot benzene. The benzene was removed under reduced pressure with gentle heating to yield a dark brown solid.

The solid material was then subjected to UV-VIS ($CH_2Cl_2$, 230-800 nm), $^1HNMR$ (133 MHz), $^{13}CNMR$, X-ray photoelectron spectroscopy (XPS) and atomic force spectroscopy. These analytical tools were used to characterize the structure of the compound produced, and such analysis indicated that the structure of the metal-ligand complex was $Au_{55}(SC_{18}H_{37})_{26}$.

X-ray photoelectron spectroscopy (XPS) data also was collected concerning $Au_{55}(SC_{18}H_{37})_{26}$. This involved irradiating molecules with high-energy photons of fixed energy. When the energy of the photons is greater than the ionization potential of an electron, the compound may eject the electron, and the kinetic energy of the electron is equal to the difference between the energy of the photons and the ionization potential. The photoelectron spectrum has sharp peaks at energies usually associated with ionization of electrons from particular orbitals. X-ray radiation generally is used to eject core electrons from materials being analyzed. Clifford E. Dykstra's *Quantum Chemistry & Molecular Spectroscopy*, pp. 296-295 (Prentice Hall, 1992). Quantification of the data provided by XPS analysis of $Au_{55}(SC_{18}H_{37})_{26}$ made according to this example showed that Au 4f comprised about 67.38% and S 2p constituted about 28.01%+4.17%, which suggests a formula of $Au_{55}(SC_{18}H_{37})_{26}$.

Quantification of XPS spectra gave a gold-to-sulfur ratio of about 2.3:1.0 and shows a complete absence of phosphorus or chlorine. As with $Au_{55}(PPh_3)_{12}Cl_6$, a broad doublet is observed for the Au 4f level. The binding energy of the Au 4f 7/2 level is about 84.0-84.2 eV versus that of adventitious carbon, 284.8 eV. This indicates absence of Au(I) and is similar to binding energies obtained for clusters such as $Au_{55}(PPh_3)_{12}Cl_6$. The binding energy of the S 2p 3/2 peak ranges from 162.4 to 162.6 eV for the series of clusters. These values are shifted to lower energy than those found for free thiols (163.3-163.9 eV) and are close to the values reported for thiolates bound to gold (162.0-162.4 eV). The possibility that unattached thiols may be present in the sample is unambiguously ruled out by $^1H$ and $^{13}C$ NMR.

Thermal gravimetric analysis confirms the Au:S ratio obtained from XPS. On heating to 600° C., ODT-stabilized clusters display a 40% mass loss, corresponding to 26 ODT ligands on an assumed 55-atom gold cluster. This ratio alludes to the retention of a small cluster size. A sample of the larger hexadecanethiol-stabilized gold cluster has been shown to give a 33.5% mass loss, corresponding to from about 95 to about 126 ligands per cluster (diameter=2.4 nm).

Figure 4:
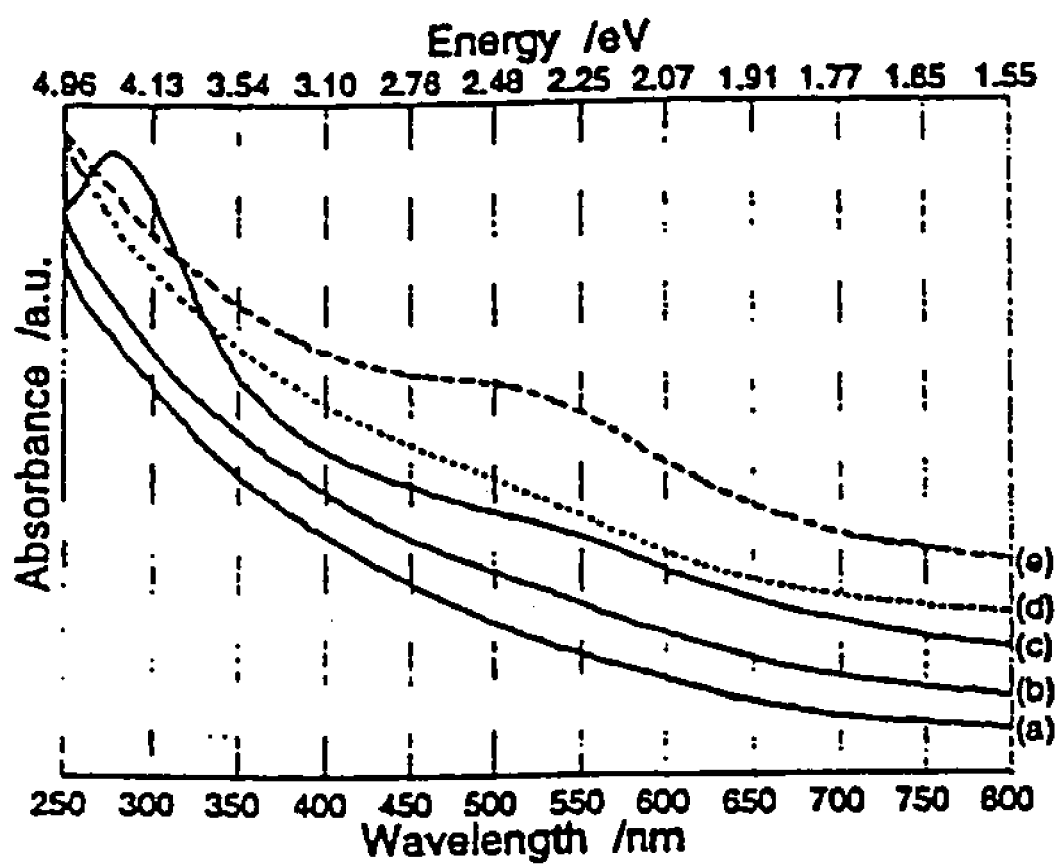
FIG. 4 is a UV-vis spectra (methylene chloride solution) of gold clusters with ligands (a) ODT, (b) Pth, and (c) MBP, and where (d) is starting material and (e) is a sample of larger ODT-stabilzed clusters.

Optical spectra of gold colloids and clusters exhibit a size-dependent surface plasmon resonance band at about 520 nm (See. FIG. 4). In absorption spectra of ligand-exchanged clusters produced as stated in this example, the interband transition typically observed for small clusters including $Au_{55}(PPh_3)_{12}Cl_6$ was observed. Little or no plasmon resonance was observed, consistent with a cluster size of about 1.7 nm or less. For the ODT-passivated cluster, no plasmon resonance was observed.

Figure 5:
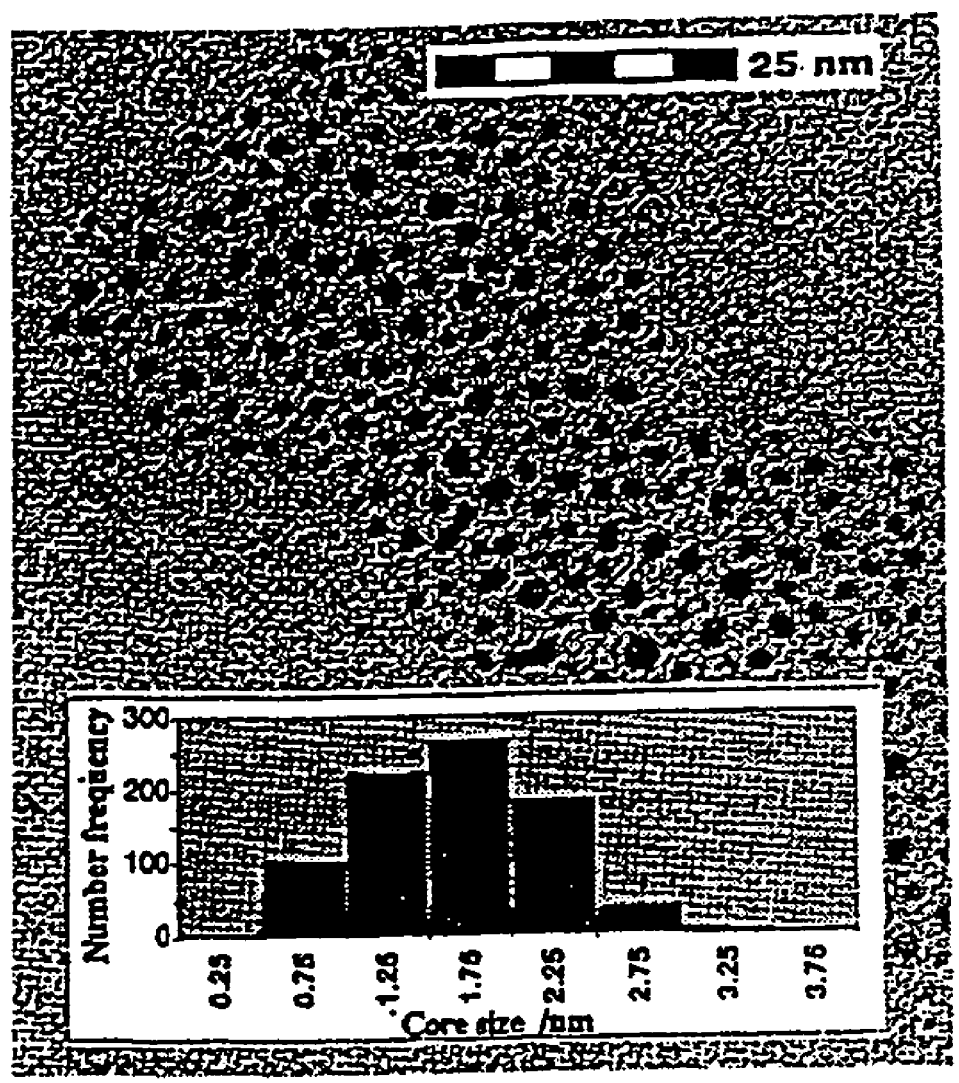
FIG. 5 is a TEM of ODT-stabilized clusters (aerosol-deposited from methylene chloride solution onto a carbon-coated copper grid).

Quantitative size information can be obtained using transmission electron microscopy (TEM). The core size obtained from TEM images of the ODT-stabilized cluster (FIG. 5) is found to be 1.7±0.5 nm and is in good agreement with that obtained from atomic force microscope images.

Atomic force microscopy (AFM) also was performed on the $Au_{55}(SC_{18}H_{37})_{26}$ produced according to this example. The analysis produced a topographical representation of the metal complex. AFM probes the surface of a sample with a sharp tip located at the free end of a cantilever. Forces between the tip and the sample surface cause the cantilever to bend or deflect. The measured cantilever deflections allow a computer to generate a map of surface topography. Rebecca Howland et al.'s *A Practical Guide to Scanning Probe Microscopy*, p. 5, (Park Scientific Instruments, 1993). The AFM data showed heights of 1.5 m for single clusters and aggregates subjected to high force. This corresponds to the size of the gold core clusters. This helped establish that the gold clusters of this example were close to the correct size for forming devices in accordance with the present invention.

In a manner similar to that described above for Example 2, thiol stabilized structures also have been made using 1-propanethiol.

Example 3

This example describes the synthesis of $Au_{55}(SPh—Ph)_x$. Dichloromethane (≈10 ml), $Au(PPh_3)_{12}Cl_6$ (25.2 mg) and 4-mercaptobiphenyl (9.60 mg) were combined in a 25 ml round bottom. A black solution was produced, and this solution was stirred under nitrogen at room temperature for 36 hours. The solvent was removed under reduced pressure and replaced with acetone. This resulted in the formation of a black powder suspension. The solid was isolated by vacuum filtration and washed with acetone (6×5 ml). The solvent was then removed under reduced pressure to yield 16.8 mg of a dark brown solid.

The solid material was subjected to UV-VIS ($CH_2Cl_2$, 230-800 nm), $^1HNMR$ (133 MHz), $^{13}CNMR$, X-ray photoelectron spectroscopy (XPS) and atomic force spectroscopy as in Example 2. This data confirmed the structure and purity of the metal complex, and further showed complete ligand exchange. For example, quantification of the XPS data made according to this example showed that Au 4f comprised about 71.02% and S 2p constituted about 28.98%, which suggests a formula of $Au_{55}(S\text{-biphenyl})_{25}$.

AFM analysis showed isolated metal clusters having measuring about 2.5 nm which correlates to the expected size of the gold core with a slightly extended sphere.

Thiol-stabilized clusters as produced above display remarkable stability relative to $Au_{55}(PPh_3)_{12}Cl_6$, which undergoes decomposition in solution at room temperature to give bulk gold and $AuCl[PPh_3]$. No decomposition for the thiol-stabilized clusters was observed, despite the fact that some samples were deliberately stored in solution for weeks. In other tests, the mercaptobiphenyl and octadecylthiol-stabilized clusters (in the absence of free thiol) were heated to 75° C. for periods of more than 9 hours in dilute 1,2-dichloroethane solution with no resultant degradation. Under identical conditions, $Au_{55}(PPh_3)_{12}Cl_6$ is observed to decompose to Au(O) and $AuCl[PPh_3]$ within 2 hours.

Example 4

This example demonstrates that polypeptide molecular templates can be used to organize small, monodisperse nanoclusters into linear arrays of molecular dimension. A $1\times10^{-8}$ M solution of poly-L-lysine is mixed with a large excess (1,000-fold) of "normal" gold 55 in methanol solution. The amino sidechains of the poly-L-lysine replace some of the labile triphenylphosphine ligands on the gold cluster and thus bind the cluster to the template. The decorated clusters precipitate out of solution onto a TEM grid. Single gold clusters that become non-specifically adsorbed on the grid will be removed by rinsing with benzene. Transmission electron micrography (TEM) analysis will show the gold cores of the cluster and will indicate the extent to which the cluster have aggregated into low-dimensional arrays due to template-induced organization.

Example 5

Figure 6:
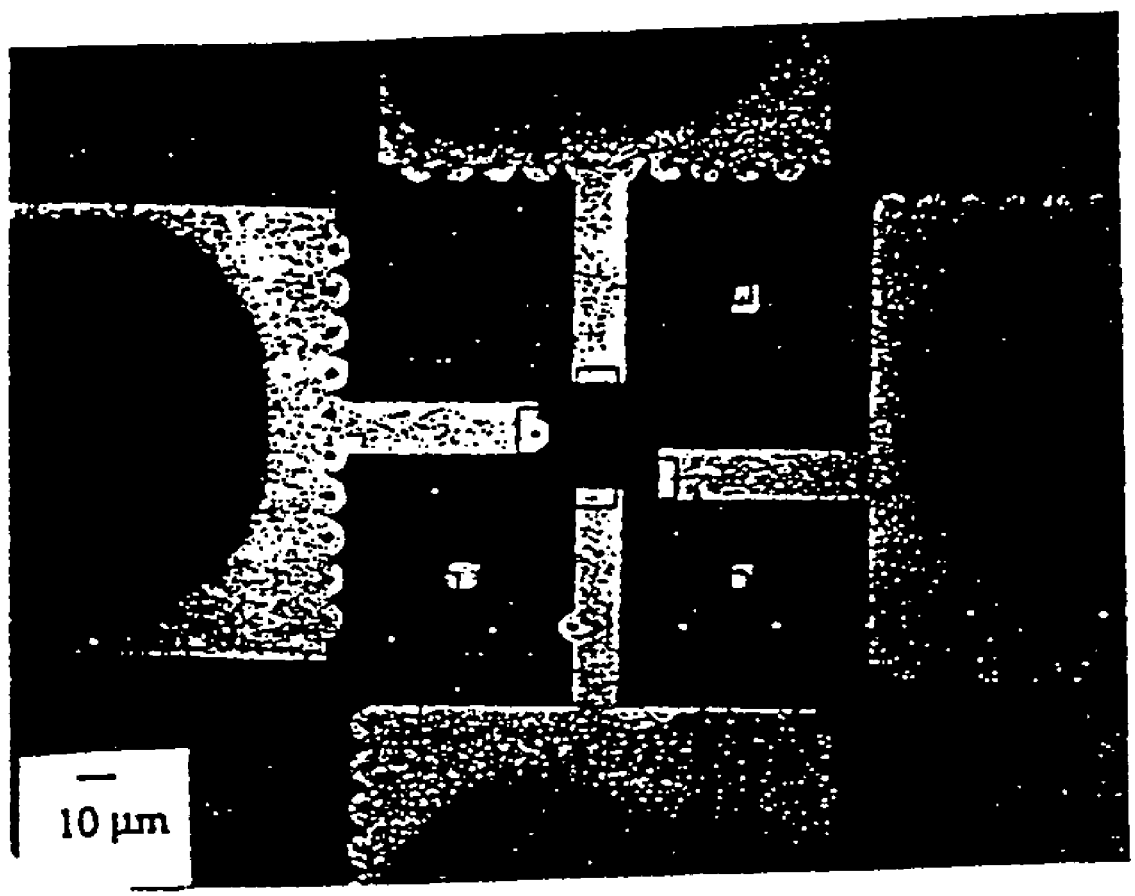
FIG. 6 is an electron micrograph of a patterned gold cluster structure.

This example describes the electron transfer properties of organometallic structures formed by electron-beam irradiation of $Au_{55}[P(C_6H_5)_3]_{12}Cl_6$. This compound was produced as stated above in Example 1. A solution of the gold cluster was made by dissolving 22 mg of the solid in 0.25 mL of $CH_2Cl_2$ and 0.25 mL of $CH_2ClCH_2Cl$. A supernatant solution was spin coated onto a $Si_3N_4$ coated Si wafer at 1500 rpm for 25 seconds immediately after preparation. The film was patterned by exposure to a 40 kV electron beam at a line dosage of 100 nC/cm. The areas of the film exposed to the electron beam adhered to the surface and a $CH_2Cl_2$ rinse removed the excess film. This procedure produced well defined structures. See, FIG. 6. These structures appeared to be smooth and continuous under SEM inspection. Attempts were made to pattern the material using 254 nm UV lithography, but it was found to be insensitive to this wavelength. The defined structures had dimensions as small as 0.1 µm and AFM inspection measured the film thickness to be 50 nm.

The organometallic samples were spin-coated with PMMA which was electron-beam exposed and developed to define contact regions. Contacts were fabricated using thermal evaporation of 100 nm of gold and conventional liftoff procedures.

DC current-voltage (I-V) measurements of several samples were taken. A shielded chamber, submerged in an oil bath, contained the sample mounted on a clean teflon stage. Rigid triaxial connections were used to connect the sample to a constant DC voltage source and electrometer. The oil bath temperature was controlled from 195 to 350K. Thermal equilibrium was achieved with a 10 Torr partial pressure of He in the chamber. Before electrical measurements the chamber was evacuated to a pressure $\approx 10^{-5}$ Torr. The data showed little temperature drift over a typical four hour measurement sweep. The intrinsic leakage current of the system was measured using a control sample which had the same substrate and contact pad arrangement as the actual samples, but did not have the organometallic between the pads. At room temperature, the leakage current was almost linearly dependent on bias over the range −100 to 100V, and had a maximum value 100 fA. While the ultimate resolution of the current measurement was 10 fA, the leakage current set the minimum resolved conductance $\approx 10^{-15}$ $\Omega^{-1}$. Constant amplitude RF signals with frequencies, $\tilde{f}$, from 0.1 to 5 MHz, were applied to the samples through a dipole antenna at 195K. No attempt was made to optimize the coupling between the RF signal and the sample.

Figure 7:
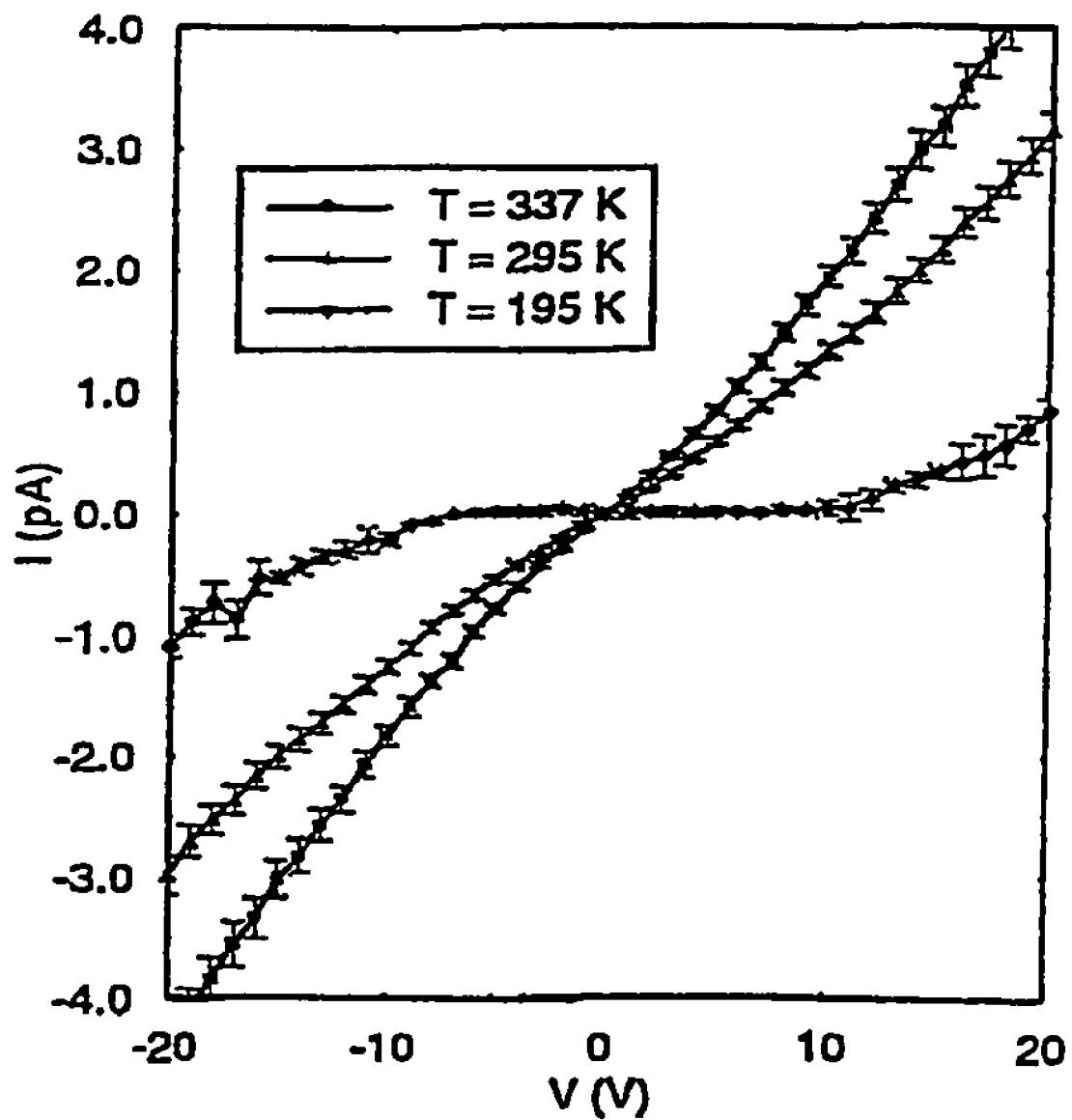
FIG. 7 is a graph illustrating current-voltage (I-V) characteristics of $Au_{55}[P(C_6H_5)_3]_{12}Cl_6$ at 195K, 295K and 337K.

Without RF, the I-V characteristics for one sample at several temperatures are shown in FIG. 7. As the temperature was reduced, the low voltage portion of the curve flattened out and the current became indistinguishable from the leakage current. Above an applied voltage magnitude of 6.7±0.6 V, the current increased abruptly. The data illustrated in FIG. 7 establishes that the monodispersed gold clusters can produce devices that operate on the basis of the Coulomb blockage effect. This can be determined from FIG. 7 because one of the curves has zero slope, indicating no current at the applied voltage, i.e., the cluster is blockaded at the particular temperature tested.

Figure 8:
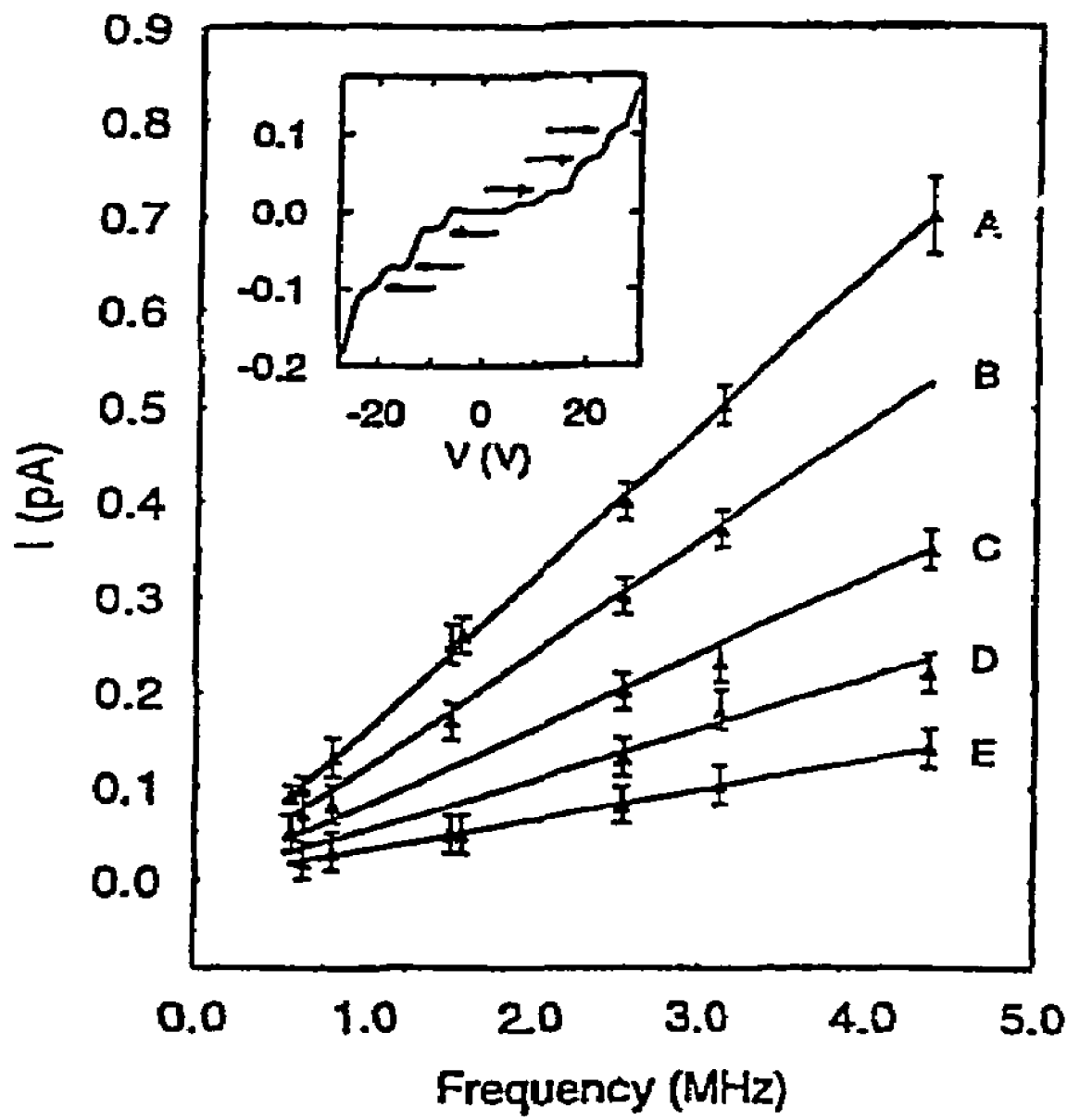
FIG. 8 is a graph illustrating observed current plateaus as a function of the applied frequency at 195K, with the inset illustrating the plateau at f=0.626 MHz.

The application of the RF signal introduced steps in the I-V characteristic, as shown in the inset to FIG. 8. FIG. 8 establishes that an applied external varying signal (the frequency of which is provided by the X axis) actually controls the rate at which electrons move through metal clusters made in accordance with the present invention. The current at which these steps occurred was found to be proportional to the applied signal frequency, as shown in FIG. 8. A least squares analysis of the linear current-frequency relationship for the highest current step shown gives a slope 1.59±0.04×10$^{-19}$ C.

The introduction of plateaus in the patterned sample I-V characteristics is similar to the RF response reported in other Coulomb blockade systems. This effect has been attributed to phase locking of single electron tunneling events by the external RF signal. When the nth harmonic of the applied frequency corresponds to the mth harmonic of the frequency of tunneling in the system, mIle, the current becomes locked to a value I=(n/m)ef. The results obtained suggest that correlated tunneling is present in the samples.

The patterned samples had stable I-V characteristics with time and temperature. Furthermore, as the temperature was raised above about 250K the I-V characteristics developed almost linear behavior up to $V_T$. The conductance below $V_T$ was activated, with activation energies $E_A$ in the range 30-70 meV. One method to estimate the charging energy from the activation energy is to use the argument that the charging energy for one island in a infinite two-dimensional array, $E_C \approx 4E_A$. Assuming current suppression requires $E_C \geq 10$ kT, the sample with the largest activation energy should develop a Coulomb gap below ~300 K. This value is within a factor of 2 of the measured temperature at which clear blockade behavior occurs in the patterned samples. Given the accuracy to which $E_c$ is known, the temperature dependence of the conductance within the Coulomb gap is consistent with the observation of blockade behavior. Using this value of $E_c$, the effective capacitance of a metal core in the patterned array is $3\times10^{-19}<C<7\times10^{-19}$F. These values are close, but larger than the classical geometric capacitance of an isolated $Au_{55}$ cluster $C=4\pi\in\in_0\tilde{r}\approx2\times10^{-19}$F, where the dielectric constant of the surrounding ligand shell $\in$ is expected to be ~3. The agreement between the two estimates of capacitance supports the notion that the current suppression in the metal cluster arrays is due to charging of individual $Au_{55}$ clusters.

The non-linear I-V characteristic is similar to that of either a forward biased diode or one-/two-dimensional arrays of ultra small metal islands or tunnel junctions. However, the dependence of the I-V characteristic on the applied RF signal is not consistent with straightforward diode behavior. Therefore, the data has been analyzed in the context of an array of ultra small metal islands.

Several reports have discussed the transport in ordered arrays of tunnel junctions that have tunneling resistances greater than the quantum resistance h/e$^2$ and a charging energy significantly above the thermal energy. In this case Coulomb blockade effects introduce a threshold voltage below which current through the array is suppressed. As the applied voltage is increased well beyond threshold, the current-voltage characteristic approaches a linear asymptote with a slope related to the tunnel resistance. With the same temperature and tunnel resistance constraints, Middleton and Wingreen have discussed one- and two-dimensional arrays of maximally disordered normal metal islands where disorder is introduced as random offset charges on each dot. These authors predict current suppression below a threshold voltage and high bias current $I \sim (V/V_T - 1)^\gamma$. Here, the threshold voltage $V_T$ scales with the number of junctions N along the current direction. Analytically $\gamma=1$ for one-dimensional systems and 5/3 for infinite two-dimensional systems. Numerical simulations of a finite two-dimensional array gave $\gamma=2.0\pm0.2$.

Figure 9:
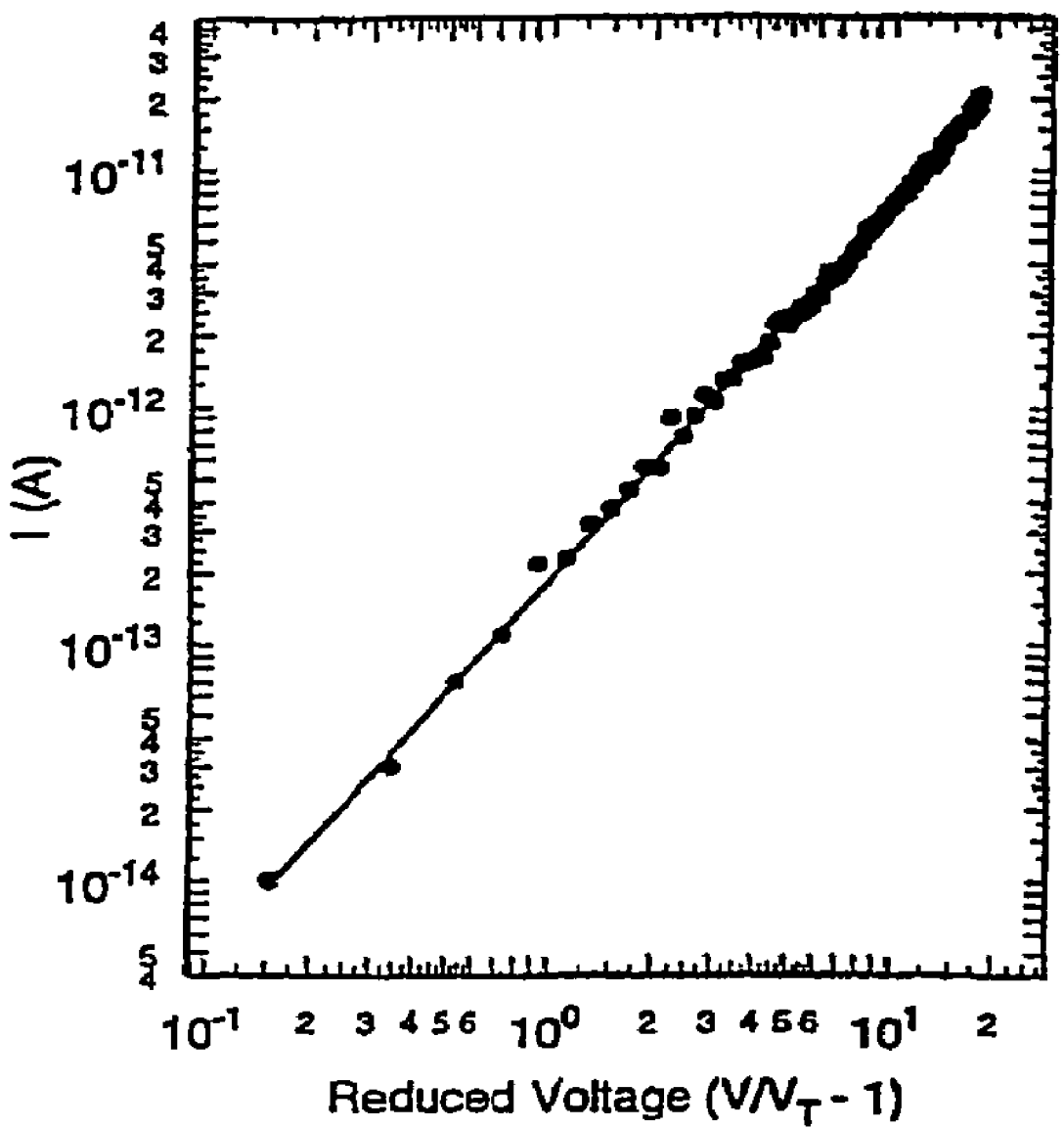
FIG. 9 is a graph illustrating current versus reduced voltage at 195K.

While no effort was made to order samples, the data was analyzed using both the ordered and the disordered models. The only consistent analysis was found to be given by the disordered model. In particular, the high bias data did not have the linear asymptote predicted for an ordered system, but did scale as expected for a disordered system, as shown in FIG. 9. FIG. 9 also shows that a two-dimensional array so that sample is propagating through the sample tested along plural parallel paths. Such an arrangement is important for developing memory storage devices. The exponent $\gamma \approx 1.6$ which is closest to the analytical prediction for an infinite, disordered two-dimensional array. From the analysis the magnitude of $V_T \sim 6\pm1$ V which is in good agreement with that estimated directly from the I-V data.

The introduction of steps in the I-V characteristics by a RF field is similar to the RF response reported in other systems. This effect has been attributed to phase locking of single electron tunneling events by the external RF signal. If the applied frequency corresponds to a rational fraction multiple of the frequency of tunneling in the system, I/e, then the current is locked to a value I=(n/m)ef, where n and m are integers. Therefore, the linear relationships shown in FIG. 6 between f and I suggests that correlated tunneling is present in the samples. The lowest slope observed is best described with n/m=⅕. For frequencies up to 3 MHz, the current resolution is insufficient to distinguish between the ⅕ and ¼ harmonics. However, at higher frequencies where it should have been possible to distinguish between ⅕ and ¼, the ¼ step was not observed.

At temperatures above about 250K, the I-V characteristic was almost linear up to $V_T$. In this regime the conductance was activated, with activation energies $E_A$ in the range 30 to 70 meV for the samples studied. Similar activated behavior has been reported for tunnel junction systems. It was argued that for an infinite 2D array the charging energy for one island $E_C \approx 4E_A$. Applying this argument to the present system, and assuming current suppression requires $E_C \geqq 10$ kT, the sample with the largest activation energy should develop a Coulomb gap below about 300 K. This estimate is within a factor of two of the measured temperature at which clear blockage behavior is seen. Thus, the temperature dependence of the observed current within the Coulomb gap is consistent with the observation of blockade behavior. From the threshold voltage, $V_T=\alpha Ne/C$, and this estimate of $E_C$, $\alpha N$ is approximately 10. The energy $E_C$ can also be estimated if the capacitance of an island is known. The capacitance of an isolated $Au_{55}$ cluster is $C=4\pi\in\in_0 r$, where r is the radius of the cluster and $\in$ is the dielectric constant of the surrounding medium. The radius of a $Au_{55}$ is 0.7 nm and the ligand shell is expected to have $\in \approx 3$, which $C \approx 2 \times 10^{-19}$F. The Coulomb charging energy, $E_C = e^2/2C \approx 340$ meV which is within twenty percent of the maximum value of $4E_A$ found from the activation data. This result suggests that the current suppression is due to charging of individual $Au_{55}$ clusters.

Given the constraint that steps in the I-V characteristics are only found when $f<0.1(R_TC)$, the fact that steps are seen up to f=5 MHz gives the upper limit $R_T<1\times10^{11}\Omega$. The differential resistance obtained from the I-V characteristic well above threshold is anticipated to be $R_{diff} \approx (N/M)R_T$, where M is the number of parallel channels. This estimate yields N/M 30. From the sample dimensions and the size of an individual cluster, a close packed array would have N/M~5. This disparity between the expected and experimentally derived values of the NIM suggests that the full width of the sample is not involved in transport. One explanation for the discrepancy in N/M may be that many of the gold cores coalesce during sample fabrication so that transport is dominated by individual clusters between larger regions of gold.

Example 6

Figure 10:
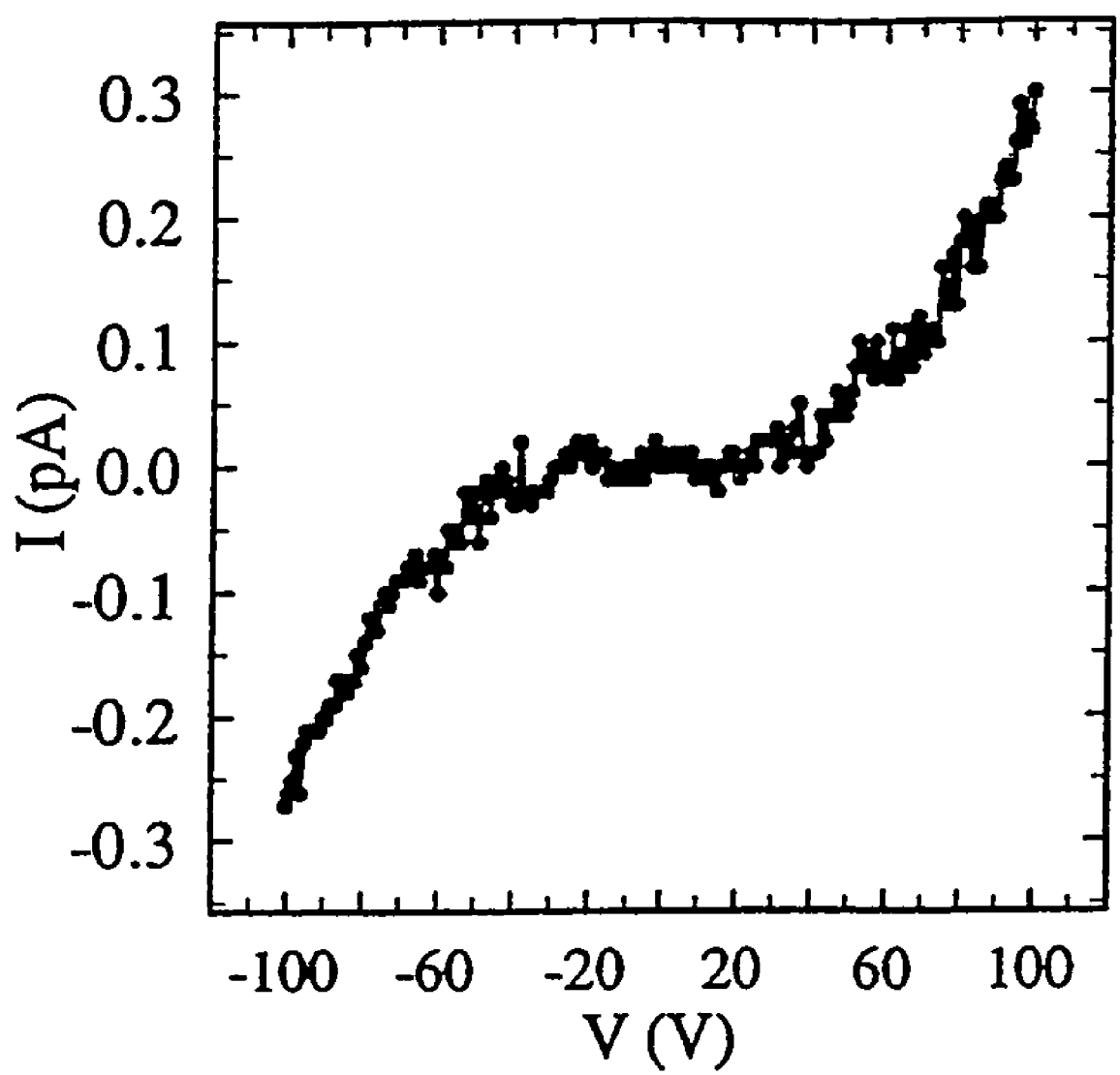
FIG. 10 is a graph illustrating current-voltage (I-V) characteristics of a poly-L-lysine scaffold decorated with 11-mercaptoundeconic ligand-stabilized gold clusters.

This example describes a method for making cluster arrays using poly-L-lysine as the scaffold and 11-mercaptoundeconic ligand-stabilized metal clusters. Prefabricated electrodes were drop-cast with a $2.2\times10^{-5}$ mol/l solution of 56,000 amu poly-L-Lysine.HBr in $H_2O/CH_3OH$. After a 20-hour soak in 1% NaOH in nanopure water and a nanopure water rinse, the current-voltage characteristics of the sample were found be be comparable with that of a bare electrode. The polylysine coated electrode was then exposed to a drop of 11-mercaptoundeconic ligand-stabilized gold clusters in DMSO (about 8 mg/1 ml). After about 20 minutes, the sample was subjected to a thorough rinse with DMSO followed by another rinse in methylene chloride. After correcting for the leakage current of the bare electrode, the current-voltage characteristic of the sample were measured, as shown in FIG. 10.

Figure 11:
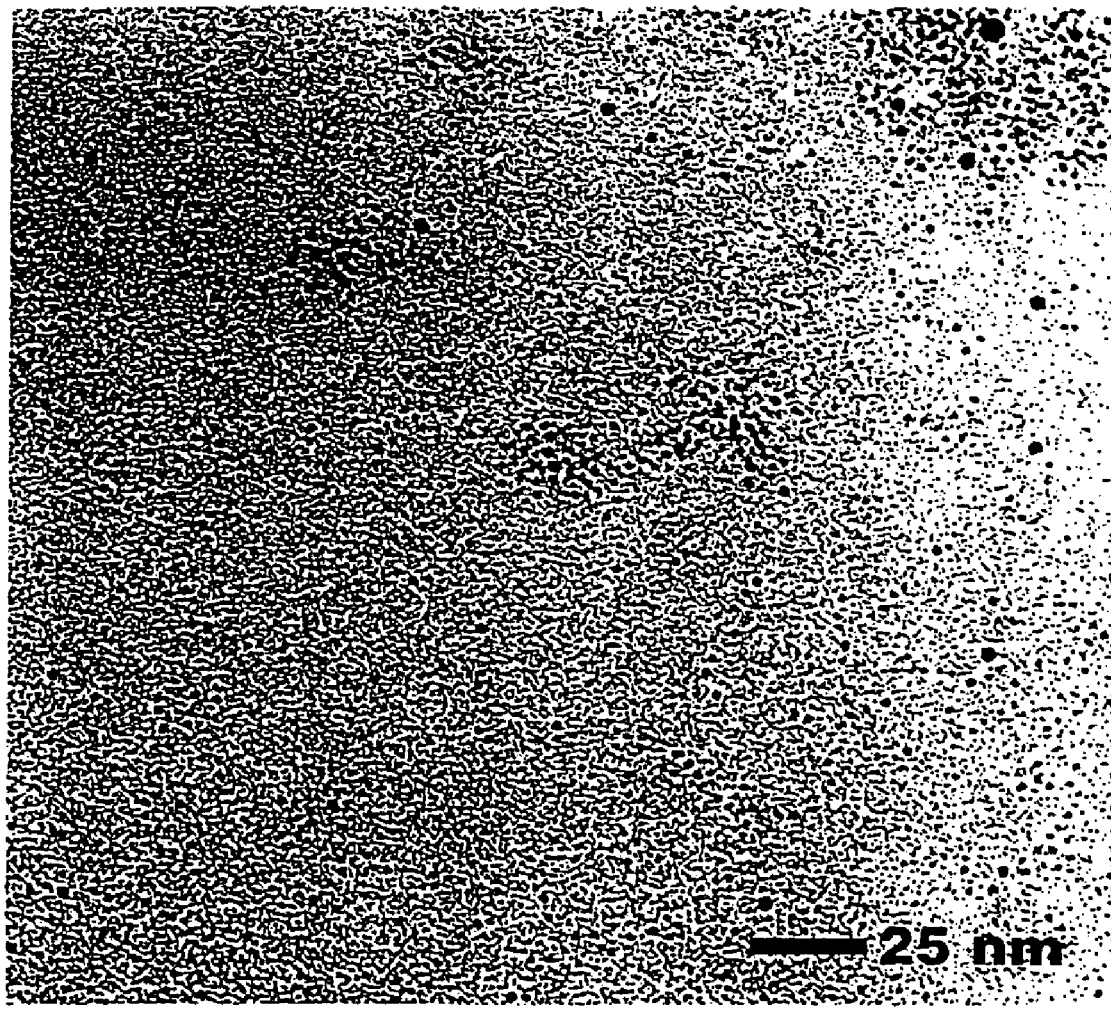
FIG. 11 is a TEM image of a TEM grid having a poly-L-lysine scaffold decorated with 11-mercaptoundeconic ligand-stabilized gold clusters.

A TEM grid was prepared as well using the polylysine scaffold and the 11-mercaptoundeconic ligand-stabilized gold clusters in DMSO. The polylysine solution was drop cast onto TEM grids. A 20-hour soak in 1% NaOH was followed by a nanopure water rinse. The dry TEM grids were then exposed to a drop of 11-mercaptoundeconic ligand-stabilized gold clusters in DMSO. After about twenty minutes, the grids were thoroughly rinsed, first using DMSO and then using methylene chloride. Lines of clusters can be seen in FIG. 11.

Example 7

This example describes how to make electrical connections to metal cluster arrays. Saw tooth interdigitated array (IDA) gold electrodes are used and are made using electron beam lithography. The gap between saw tooth points in the array will be approximately 200-300 Angstroms. An omega-amino alkanethiol will be chemisorbed to the gold surface and subsequently electrochemically desorbed from one set of the IDA fingers. An omega-NHS-ester alkylthiol will be attached to the bare set of fingers. A precursor to poly-L-lysine will be polymerized from the amino-modified fingers toward the NHS-ester fingers where the growing end will be captured. The side chains of the poly-L-lysine chain will be deprotected and treated with carboxy-terminated gold nanoparticles to form the desired one-dimensional array. Gates will be incorporated either under the substrate or as an additional electrode near (above) the surface of the device.

The present invention has been described with reference to preferred embodiments. Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. An array of metal clusters, comprising:
   a substrate;
   monodispersed, thiol-stabilized gold clusters having metal-cluster radiuses of from about 0.7 nm to about 1.8 nm; and
   a polylysine scaffold having a lateral definition of about 10 Å coupled to the substrate, in predetermined patterns on the substrate; and a plurality of gold clusters being coupled to the scaffold, the clusters having a distance between the edges of cluster cores of less than about 5 nm.

2. The array of claim 1, wherein the distance between the edges of cluster cores is from about 1 nm to about 5 nm.

3. An array, comprising:
   a substrate;
   a polylysine scaffold coupled to the substrate; and
   a plurality of gold clusters coupled to the scaffold with an interparticle separation of less than about 5 nm, the gold clusters having at least one thiol ligand coordinated thereto, and
   the clusters having metal-cluster radiuses of from about 0.7 nm to about 1.8 nm.

4. The array of claim 3, wherein the gold clusters are electrostatically coupled to the scaffold.

5. The array of claim 3, wherein the thiol ligand comprises an aryl group, an alkyl group, or both.

6. The array of claim 5, wherein the thiol ligand comprises an acidic group.

7. The array of claim 6, wherein the acidic group is a carboxylic acid group.

8. The array of claim 7, wherein the thiol ligand is selected from thiopropionic acid or mercaptoundecanoic acid.

9. The array of claim 3, wherein the substrate comprises silicon, silicon nitride, ultraflat glass, gold or a combination thereof.

10. The array of claim 3, wherein the scaffold has a lateral definition of about 10 Å.

11. The array of claim 3, wherein the distance between the edges of cluster cores is from about 1 nm to about 5 nm.

* * * * *